(12) United States Patent
Kramer et al.

(10) Patent No.: US 9,486,633 B2
(45) Date of Patent: Nov. 8, 2016

(54) SELECTIVE STIMULATION TO MODULATE THE SYMPATHETIC NERVOUS SYSTEM

(71) Applicants: The Board of Trustees of the Leland Stanford Junior University, Stanford, CA (US); St. Jude Medical Luxembourg Holdings SMI S.A.R.L. ("SJM LUX SMI"), Luxembourg (LU)

(72) Inventors: Jeffery M. Kramer, San Francisco, CA (US); Daniel H. Kim, Houston, TX (US); Mir A. Imran, Los Altos, CA (US)

(73) Assignees: The Board of Trustees of the Leland Stanford Junior University, Stanford, CA (US); St. Jude Medical Luxembourg Holdings SMI S.A.R.L. ("SJM LUX SMI"), Luxembourg (LU)

(*) Notice: Subject to any disclaimer, the term of this patent is extended or adjusted under 35 U.S.C. 154(b) by 0 days.

(21) Appl. No.: 14/954,740

(22) Filed: Nov. 30, 2015

(65) Prior Publication Data

US 2016/0082258 A1 Mar. 24, 2016

Related U.S. Application Data

(60) Continuation of application No. 13/458,697, filed on Apr. 27, 2012, now abandoned, and a continuation-in-part of application No. 12/369,706, filed on Feb. 11, 2009, now Pat. No. 8,229,565, which (Continued)

(51) Int. Cl.
*A61N 1/36* (2006.01)
*A61N 1/05* (2006.01)

(52) U.S. Cl.
CPC ......... *A61N 1/36114* (2013.01); *A61N 1/0551* (2013.01); *A61N 1/36057* (2013.01); *A61N 1/36071* (2013.01); *A61N 1/36135* (2013.01)

(58) Field of Classification Search
CPC ............. A61N 1/3601; A61N 1/0551; A61N 1/0553; A61N 1/0556; A61N 1/362; A61N 1/3627
USPC .......................................................... 607/39
See application file for complete search history.

(56) References Cited

U.S. PATENT DOCUMENTS

| 525,891 A | 9/1894 | Fricke |
| 3,724,467 A | 4/1973 | Avery et al. |

(Continued)

FOREIGN PATENT DOCUMENTS

| CN | 2401143 Y | 10/2000 |
| CN | 101594907 A | 12/2009 |

(Continued)

OTHER PUBLICATIONS

PDF of the Medscape definition of Angina Pectoris http://emedicine.medscape.com/article/150215-overview.*

(Continued)

*Primary Examiner* — Paula J Stice
(74) *Attorney, Agent, or Firm* — Shay Glenn LLP

(57) ABSTRACT

Systems, methods and devices are provided for the targeted treatment of a variety of medical conditions by directly neuromodulating a target anatomy associated with the condition while minimizing or excluding undesired neuromodulation of other anatomies. Typically, the target anatomy includes one or more dorsal root ganglia, dorsal roots, dorsal root entry zones, or portions thereof. Such target stimulation areas are utilized due in part to their effect on the sympathetic nervous system.

9 Claims, 7 Drawing Sheets

Related U.S. Application Data is a division of application No. 11/222,516, filed on Sep. 7, 2005, now Pat. No. 7,502,651.

(60) Provisional application No. 61/480,958, filed on Apr. 29, 2011, provisional application No. 60/608,357, filed on Sep. 8, 2004.

(56) References Cited

U.S. PATENT DOCUMENTS

| | | | |
|---|---|---|---|
| 3,845,770 A | 11/1974 | Theeuwes et al. | |
| 3,916,899 A | 11/1975 | Theeuwes et al. | |
| 4,141,367 A | 2/1979 | Ferreira | |
| 4,232,679 A | 11/1980 | Schulman | |
| 4,298,003 A | 11/1981 | Theeuwes et al. | |
| 4,313,448 A | 2/1982 | Stokes | |
| 4,374,527 A | 2/1983 | Iversen | |
| 4,479,491 A | 10/1984 | Martin | |
| 4,549,556 A | 10/1985 | Tarjan et al. | |
| 4,573,481 A | 3/1986 | Bullara | |
| 4,577,642 A | 3/1986 | Stokes | |
| 4,590,946 A | 5/1986 | Loeb | |
| 4,607,639 A | 8/1986 | Tanagho et al. | |
| 4,739,764 A | 4/1988 | Lue et al. | |
| 4,786,155 A | 11/1988 | Fantone et al. | |
| 4,803,988 A | 2/1989 | Thomson | |
| 4,920,979 A | 5/1990 | Bullara | |
| 4,940,065 A | 7/1990 | Tanagho et al. | |
| 4,950,270 A | 8/1990 | Bowman et al. | |
| 4,976,711 A | 12/1990 | Parins et al. | |
| 5,135,525 A | 8/1992 | Biscoping et al. | |
| 5,270,099 A | 12/1993 | Kamiyama et al. | |
| 5,299,569 A | 4/1994 | Wernicke et al. | |
| 5,344,438 A | 9/1994 | Testerman et al. | |
| 5,358,514 A | 10/1994 | Schulman et al. | |
| 5,370,644 A | 12/1994 | Langberg | |
| 5,411,537 A | 5/1995 | Munshi et al. | |
| 5,411,540 A | 5/1995 | Edell et al. | |
| 5,417,719 A | 5/1995 | Hull et al. | |
| 5,419,763 A | 5/1995 | Hildebrand | |
| 5,458,626 A | 10/1995 | Krause | |
| 5,489,294 A | 2/1996 | McVenes et al. | |
| 5,505,201 A | 4/1996 | Grill et al. | |
| 5,514,175 A | 5/1996 | Kim et al. | |
| 5,584,835 A | 12/1996 | Greenfield | |
| 5,634,462 A | 6/1997 | Tyler et al. | |
| 5,643,330 A | 7/1997 | Holsheimer et al. | |
| 5,702,429 A | 12/1997 | King | |
| 5,711,316 A | 1/1998 | Elsberry et al. | |
| 5,713,922 A | 2/1998 | King | |
| 5,733,322 A | 3/1998 | Starkebaum | |
| 5,741,319 A | 4/1998 | Woloszko et al. | |
| 5,755,750 A | 5/1998 | Petruska et al. | |
| 5,776,170 A | 7/1998 | MacDonald et al. | |
| 5,807,339 A | 9/1998 | Bostrom et al. | |
| 5,824,021 A | 10/1998 | Rise | |
| 5,865,843 A | 2/1999 | Baudino | |
| 5,871,531 A | 2/1999 | Struble | |
| 5,885,290 A | 3/1999 | Guerrero et al. | |
| 5,938,690 A | 8/1999 | Law et al. | |
| 5,948,007 A | 9/1999 | Starkebaum et al. | |
| 5,957,965 A | 9/1999 | Moumane et al. | |
| 5,983,141 A | 11/1999 | Sluijter et al. | |
| 5,984,896 A | 11/1999 | Boyd | |
| 6,002,964 A | 12/1999 | Feler et al. | |
| 6,044,297 A | 3/2000 | Sheldon et al. | |
| 6,045,532 A | 4/2000 | Eggers et al. | |
| 6,051,017 A | 4/2000 | Loeb et al. | |
| 6,104,957 A * | 8/2000 | Alo | A61N 1/0551 128/898 |
| 6,120,467 A | 9/2000 | Schallhorn | |
| 6,161,048 A | 12/2000 | Sluijter et al. | |
| 6,175,764 B1 | 1/2001 | Loeb et al. | |
| 6,181,965 B1 | 1/2001 | Loeb et al. | |
| 6,185,455 B1 | 2/2001 | Loeb et al. | |
| 6,205,359 B1 | 3/2001 | Boveja | |
| 6,208,902 B1 | 3/2001 | Boveja | |
| 6,214,016 B1 | 4/2001 | Williams et al. | |
| 6,259,952 B1 | 7/2001 | Sluijter et al. | |
| 6,298,256 B1 | 10/2001 | Meyer | |
| 6,314,325 B1 | 11/2001 | Fitz | |
| 6,319,241 B1 | 11/2001 | King et al. | |
| 6,349,233 B1 | 2/2002 | Adams | |
| 6,353,762 B1 | 3/2002 | Baudino et al. | |
| 6,356,786 B1 | 3/2002 | Rezai et al. | |
| 6,360,750 B1 | 3/2002 | Gerber et al. | |
| 6,366,814 B1 | 4/2002 | Boveja et al. | |
| 6,393,325 B1 | 5/2002 | Mann et al. | |
| 6,413,255 B1 | 7/2002 | Stern | |
| 6,425,887 B1 | 7/2002 | McGuckin et al. | |
| 6,438,423 B1 | 8/2002 | Rezai et al. | |
| 6,440,090 B1 | 8/2002 | Schallhorn | |
| 6,466,821 B1 | 10/2002 | Pianca et al. | |
| 6,493,588 B1 | 12/2002 | Malaney et al. | |
| 6,510,347 B2 | 1/2003 | Borkan | |
| 6,512,958 B1 | 1/2003 | Swoyer et al. | |
| 6,516,227 B1 | 2/2003 | Meadows et al. | |
| 6,517,542 B1 | 2/2003 | Papay et al. | |
| 6,522,926 B1 | 2/2003 | Kieval et al. | |
| 6,535,767 B1 | 3/2003 | Kronberg | |
| 6,582,441 B1 | 6/2003 | He et al. | |
| 6,587,725 B1 | 7/2003 | Durand et al. | |
| 6,605,094 B1 | 8/2003 | Mann et al. | |
| 6,606,521 B2 | 8/2003 | Paspa et al. | |
| 6,611,715 B1 | 8/2003 | Boveja | |
| 6,625,496 B1 | 9/2003 | Ollivier | |
| 6,638,276 B2 | 10/2003 | Sharkey et al. | |
| 6,658,302 B1 | 12/2003 | Kuzma et al. | |
| 6,714,822 B2 | 3/2004 | King et al. | |
| 6,748,276 B1 | 6/2004 | Daignault, Jr. et al. | |
| 6,754,539 B1 | 6/2004 | Erickson et al. | |
| 6,788,975 B1 | 9/2004 | Whitehurst et al. | |
| 6,792,318 B2 | 9/2004 | Chitre et al. | |
| 6,832,115 B2 | 12/2004 | Borkan | |
| 6,835,194 B2 | 12/2004 | Johnson et al. | |
| 6,839,588 B1 | 1/2005 | Rudy | |
| 6,849,075 B2 | 2/2005 | Bertolero et al. | |
| 6,862,479 B1 * | 3/2005 | Whitehurst | A61N 1/32 604/503 |
| 6,871,099 B1 | 3/2005 | Whitehurst et al. | |
| 6,873,342 B2 | 3/2005 | Perry et al. | |
| 6,889,094 B1 | 5/2005 | Kuzma et al. | |
| 6,901,287 B2 | 5/2005 | Davis et al. | |
| 6,902,547 B2 | 6/2005 | Aves et al. | |
| 6,909,917 B2 | 6/2005 | Woods et al. | |
| 6,928,320 B2 | 8/2005 | King | |
| 6,971,391 B1 | 12/2005 | Wang et al. | |
| 6,978,180 B2 | 12/2005 | Tadlock | |
| 7,047,082 B1 | 5/2006 | Schrom et al. | |
| 7,096,070 B1 | 8/2006 | Jenkins et al. | |
| 7,127,287 B2 | 10/2006 | Duncan et al. | |
| 7,181,289 B2 | 2/2007 | Pflueger et al. | |
| 7,333,857 B2 | 2/2008 | Campbell | |
| 7,337,005 B2 | 2/2008 | Kim et al. | |
| 7,337,006 B2 | 2/2008 | Kim et al. | |
| 7,447,546 B2 | 11/2008 | Kim et al. | |
| 7,450,993 B2 | 11/2008 | Kim et al. | |
| 7,502,651 B2 | 3/2009 | Kim et al. | |
| 7,580,753 B2 | 8/2009 | Kim et al. | |
| 8,082,039 B2 | 12/2011 | Kim et al. | |
| 8,229,565 B2 | 7/2012 | Kim et al. | |
| 8,380,318 B2 | 2/2013 | Kishawi et al. | |
| 8,518,092 B2 | 8/2013 | Burdulis | |
| 8,712,546 B2 | 4/2014 | Kim et al. | |
| 8,983,624 B2 | 3/2015 | Imran | |
| 9,044,592 B2 | 6/2015 | Imran et al. | |
| 9,056,197 B2 | 6/2015 | Imran et al. | |
| 9,205,259 B2 | 12/2015 | Kim et al. | |
| 9,205,260 B2 | 12/2015 | Kim et al. | |
| 9,205,261 B2 | 12/2015 | Kim et al. | |
| 2001/0003799 A1 | 6/2001 | Boveja | |
| 2001/0006967 A1 | 7/2001 | Crain et al. | |
| 2002/0064841 A1 | 5/2002 | Klemic et al. | |
| 2002/0077684 A1 | 6/2002 | Clemens et al. | |
| 2002/0087113 A1 | 7/2002 | Hartlaub | |

(56) References Cited

U.S. PATENT DOCUMENTS

| | | |
|---|---|---|
| 2002/0099430 A1 | 7/2002 | Verness |
| 2002/0116030 A1 | 8/2002 | Rezai |
| 2002/0128694 A1 | 9/2002 | Holsheimer |
| 2002/0147486 A1 | 10/2002 | Soukup et al. |
| 2002/0198527 A1 | 12/2002 | Muckter |
| 2003/0018367 A1 | 1/2003 | DiLorenzo |
| 2003/0023241 A1 | 1/2003 | Drewry et al. |
| 2003/0045919 A1 | 3/2003 | Swoyer et al. |
| 2003/0069569 A1 | 4/2003 | Burdette et al. |
| 2003/0078633 A1 | 4/2003 | Firlik et al. |
| 2003/0088301 A1 | 5/2003 | King |
| 2003/0100933 A1 | 5/2003 | Ayal et al. |
| 2003/0114905 A1 | 6/2003 | Kuzma |
| 2003/0130577 A1 | 7/2003 | Purdy et al. |
| 2003/0144657 A1 | 7/2003 | Bowe et al. |
| 2003/0144709 A1 | 7/2003 | Zabara et al. |
| 2003/0181958 A1 | 9/2003 | Dobak, III |
| 2003/0187490 A1 | 10/2003 | Gliner |
| 2003/0195602 A1 | 10/2003 | Boling |
| 2003/0220677 A1 | 11/2003 | Doan et al. |
| 2004/0015202 A1 | 1/2004 | Chandler et al. |
| 2004/0019359 A1 | 1/2004 | Worley et al. |
| 2004/0019369 A1 | 1/2004 | Duncan et al. |
| 2004/0059404 A1 | 3/2004 | Bjorklund et al. |
| 2004/0116977 A1 | 6/2004 | Finch et al. |
| 2004/0122360 A1 | 6/2004 | Waldhauser et al. |
| 2004/0122477 A1* | 6/2004 | Whitehurst ........ A61N 1/36114 607/9 |
| 2004/0122497 A1 | 6/2004 | Zhang et al. |
| 2004/0122498 A1 | 6/2004 | Zhang et al. |
| 2004/0147992 A1 | 7/2004 | Bluger et al. |
| 2004/0210290 A1 | 10/2004 | Omar-Pasha |
| 2004/0215286 A1 | 10/2004 | Stypulkowski |
| 2004/0230273 A1 | 11/2004 | Cates et al. |
| 2004/0230280 A1 | 11/2004 | Cates et al. |
| 2004/0243210 A1 | 12/2004 | Morgan et al. |
| 2005/0027338 A1 | 2/2005 | Hill |
| 2005/0033295 A1 | 2/2005 | Wisnewski |
| 2005/0033393 A1 | 2/2005 | Daglow |
| 2005/0038489 A1 | 2/2005 | Grill |
| 2005/0070982 A1 | 3/2005 | Heruth et al. |
| 2005/0080325 A1 | 4/2005 | Erickson |
| 2005/0090885 A1 | 4/2005 | Harris et al. |
| 2005/0096718 A1 | 5/2005 | Gerber et al. |
| 2005/0149154 A1 | 7/2005 | Cohen et al. |
| 2005/0154437 A1 | 7/2005 | Williams |
| 2005/0159799 A1 | 7/2005 | Daglow et al. |
| 2005/0203599 A1 | 9/2005 | Garabedian et al. |
| 2005/0222647 A1 | 10/2005 | Wahlstrand et al. |
| 2005/0251237 A1 | 11/2005 | Kuzma et al. |
| 2006/0004364 A1 | 1/2006 | Green et al. |
| 2006/0009820 A1 | 1/2006 | Royle |
| 2006/0041295 A1 | 2/2006 | Osypka |
| 2006/0052836 A1 | 3/2006 | Kim et al. |
| 2006/0052856 A1 | 3/2006 | Kim et al. |
| 2006/0064150 A1 | 3/2006 | Heist et al. |
| 2006/0089609 A1 | 4/2006 | Bleich et al. |
| 2006/0089696 A1 | 4/2006 | Olsen et al. |
| 2006/0094976 A1 | 5/2006 | Bleich |
| 2006/0095088 A1 | 5/2006 | DeRidder |
| 2006/0155344 A1 | 7/2006 | Rezai et al. |
| 2006/0161235 A1 | 7/2006 | King |
| 2006/0167525 A1 | 7/2006 | King |
| 2006/0195169 A1 | 8/2006 | Gross et al. |
| 2006/0200121 A1 | 9/2006 | Mowery |
| 2006/0206118 A1 | 9/2006 | Kim et al. |
| 2006/0241716 A1 | 10/2006 | Finch et al. |
| 2006/0247750 A1 | 11/2006 | Seifert et al. |
| 2007/0043400 A1 | 2/2007 | Donders et al. |
| 2007/0060954 A1 | 3/2007 | Cameron et al. |
| 2007/0123954 A1 | 5/2007 | Gielen et al. |
| 2007/0179579 A1 | 8/2007 | Feler et al. |
| 2007/0213671 A1 | 9/2007 | Hiatt |
| 2007/0255366 A1 | 11/2007 | Gerber et al. |
| 2007/0270928 A1 | 11/2007 | Erlebacher |
| 2007/0276319 A1 | 11/2007 | Betts |
| 2008/0009927 A1 | 1/2008 | Vilims |
| 2008/0033431 A1 | 2/2008 | Jung et al. |
| 2008/0039916 A1 | 2/2008 | Colliou et al. |
| 2008/0103572 A1 | 5/2008 | Gerber |
| 2008/0103579 A1 | 5/2008 | Gerber |
| 2008/0103580 A1 | 5/2008 | Gerber |
| 2008/0119711 A1 | 5/2008 | Nikumb et al. |
| 2008/0140152 A1 | 6/2008 | Imran et al. |
| 2008/0140153 A1 | 6/2008 | Burdulis |
| 2008/0147156 A1 | 6/2008 | Imran |
| 2008/0154349 A1 | 6/2008 | Rossing et al. |
| 2008/0183221 A1 | 7/2008 | Burdulis |
| 2008/0188916 A1 | 8/2008 | Jones et al. |
| 2009/0204173 A1 | 8/2009 | Fang et al. |
| 2009/0248095 A1 | 10/2009 | Schleicher et al. |
| 2009/0270960 A1 | 10/2009 | Zhao et al. |
| 2009/0299444 A1 | 12/2009 | Boling |
| 2010/0121408 A1 | 5/2010 | Imran et al. |
| 2010/0179562 A1 | 7/2010 | Linker et al. |
| 2010/0191307 A1 | 7/2010 | Fang et al. |
| 2010/0292769 A1 | 11/2010 | Brounstein et al. |
| 2011/0184486 A1 | 7/2011 | De Ridder |
| 2011/0276056 A1 | 11/2011 | Grigsby et al. |
| 2012/0158094 A1 | 6/2012 | Kramer et al. |
| 2012/0277839 A1 | 11/2012 | Kramer et al. |
| 2012/0283800 A1 | 11/2012 | Perryman et al. |
| 2012/0310140 A1 | 12/2012 | Kramer et al. |
| 2012/0330384 A1 | 12/2012 | Perryman et al. |
| 2013/0066400 A1 | 3/2013 | Perryman et al. |
| 2013/0079849 A1 | 3/2013 | Perryman et al. |
| 2013/0345783 A1 | 12/2013 | Burdulis |
| 2014/0031837 A1 | 1/2014 | Perryman et al. |
| 2014/0200625 A1 | 7/2014 | Kim et al. |
| 2014/0343624 A1 | 11/2014 | Kramer |
| 2015/0151126 A1 | 6/2015 | Kishawi et al. |
| 2015/0165193 A1 | 6/2015 | Imran |
| 2015/0251004 A1 | 9/2015 | Imran et al. |
| 2015/0258338 A1 | 9/2015 | Kishawi et al. |
| 2015/0343206 A1 | 12/2015 | Burdulis |

FOREIGN PATENT DOCUMENTS

| | | |
|---|---|---|
| CN | 101678204 A | 3/2010 |
| EP | 0779080 A | 6/1997 |
| EP | 1304135 A2 | 4/2003 |
| EP | 2756864 A1 | 7/2014 |
| JP | 03041191 B2 | 6/1991 |
| JP | H06-218064 A | 8/1994 |
| JP | 8500996 A | 2/1996 |
| JP | 8080353 A | 3/1996 |
| JP | 10243954 A | 9/1998 |
| JP | 2004512105 | 4/2004 |
| JP | 2006523215 | 10/2004 |
| JP | 2005516697 | 6/2005 |
| JP | 2006508768 | 3/2006 |
| JP | 2008526299 | 7/2008 |
| JP | 2009539425 | 11/2009 |
| JP | 2009539426 | 11/2009 |
| WO | WO 02/096512 A1 | 12/2002 |
| WO | WO 03/018113 A1 | 3/2003 |
| WO | WO 03/043690 A1 | 5/2003 |
| WO | WO 03/063692 A2 | 8/2003 |
| WO | WO 03/066154 A2 | 8/2003 |
| WO | WO 03/084433 A2 | 10/2003 |
| WO | WO 03/090599 A2 | 11/2003 |
| WO | WO 2005/092432 A1 | 10/2005 |
| WO | WO 2006/033039 A1 | 3/2006 |
| WO | WO 2006/084635 A2 | 8/2006 |
| WO | WO 2009/134350 A2 | 11/2009 |
| WO | WO2013/019757 A2 | 2/2013 |
| WO | WO2013/025632 A1 | 2/2013 |

OTHER PUBLICATIONS

Abdulla et al.; Axotomy- and autotomy-induced changes in the excitability of rat dorsal root ganglion neurons; J Neurophysiol; 85(2); pp. 630-643; Feb. 2001.

(56) References Cited

OTHER PUBLICATIONS

Advanced Neuromodulation Systems, Inc. (ANSI) Research Briefing dated Aug. 20, 2004 by Stephens Inc. Investment Bankers pp. 1-4.
Advanced Neuromodulation Systems, Inc. (ANSI) Research Bulletin dated Jul. 2, 2004 by Stephens Inc. Investment Bankers pp. 1-7.
Advanced Neuromodulation Systems, Inc. (ANSI) Research Bulletin dated Jul. 27, 2004 by Stephens Inc. Investment Bankers pp. 1-9.
Advanced Neuromodulation Systems, Inc. Equity Research dated Jan. 16, 2003 by Pacific Growth Equities pp. 1-8.
Alo, Kenneth M. New Trends in Neuromodulation for the Management of Neuropathic Pain. Neurosurgery. 50 (4): 690-703. Apr. 2002.
Aoki, Yasuchika et al. Distribution and Immunocytochemical Characterization of Dorsal Root Ganglion Neurons Innervating the Lumbar Intervertebral Disc in Rats: A Review. Life Sciences. 74 (21): 2627-2642. Apr. 2004.
Askar, Zahid, et al. Scott Wiring for Direct Repair of Lumbar Spondylolysis. Spine. . 28 (4): 354-357. Feb. 2003.
Baba, Hiroshi et al. Peripheral Inflammation Facilitates A? Fiber-Mediated Synaptic Input to the Substantia Gelatinosa of the Adult Rat Spinal Cord. The Journal of Neuroscience. 19 (2): 859-867. Jan. 1999.
Bajwa, Zahid H. et al. Herpetic Neuralgia: Use of Combination Therapy for Pain Relief in Acute and Chronic Herpes Zoster. Geriatrics. 56 (12): 18-24. Dec. 2001.
Barendse, G.A. et al. Randomized Controlled Trial of Percutaneous Intradiscal Radiofrequency Thermocoagulation for Chronic Discogenic Back Pain: Lack of Effect From a 90-Second 70 C Lesion. Spine. 26 (3): 287-92. (Abstract Only). Feb. 1, 2001.
Barlocher, C.B. et al. Kryorhizotomy: An Alternative Technique for Lumbar Medial Branch Rhizotomy in Lumbar Facet Syndrome. J Neurosurg. 98 (1): 14-20. (Abstract Only). Jan. 2003.
Blau, A. et al. Characterization and Optimization of Microelectrode Arrays for In Vivo Nerve Signal Recording and Stimulation. Biosens Bioelectron. 12 (9-10): 883-92. (Abstract Only). Nov. 1997.
Boston Scientific A Neuromodulation Primer dated Jun. 9, 2004 in Medical Supplies and Devices, published by Susquehanna Financial Group, LLLP pp. 1-17.
Brammah, T.B. et al. . Syringomyelia as a Complication of Spinal Arachnoiditis. Spine. 19 (22): 2603-5. (Abstract Only). Nov. 15, 1994.
Braverman D.L. et al. Using Gabapentin to Treat Failed Back Surgery Syndrome Caused by Epidural Fibrosis: A Report of 2 Cases. Arch Phys Med Rehabil. 82 (5): 691-3. (Abstract Only). May 2001.
Burton et al.; The organization of the seventh lumbar spinal ganglion of the cat; J Comp Neurol.; 149(2); pp. 215-232; May 15, 1973.
Carlton, Susan M. et al. Tonic Control of Peripheral Cutaneous Nociceptors by Somatostatin Receptors. Journal of Neuroscience. 21 (11): 4042-4049. Jun. 1, 2001.
Chaplan, S.R. et al. Quantitative Assessment of Tactile Allodynia in the Rat Paw. Journal of Neuroscience Methods. 53 (1): 55-63. Jul. 1994.
Cho, J. Percutaneo Radiofrequency Lumbar Facet Rhizotomy in Mechanical Low Back Pain Syndrome. Stereotact Funct Neurosurg. 68 (1-4): 212-7. (Abstract Only). (year of pub. sufficiently earlier than effective US filing date and any foreign priority date) 1997.
Cipolla—The Cerebral Circulation,Chap. 3-Perivascular Innervation ; Morgan & Claypool Life Sciences; San Rafael, Ca.; 1(1):pp. 3; Jan. 2009.
Clark, Robert K. "Anatomy and physiology: understanding the human body"; Jones & Bartlett Publishers; Sudbury, MA; ISBN 0-7637-4816-6; Chapter 12; pp. 213-215; Feb. 28, 2005.
Crampon, M.-A. et al. Nerve Cuff Electrode With Shape Memory Alloy Armature: Design and Fabrication. Bio-Medical Materials and Engineering. 12 (4): 397-410. (year of pub. sufficiently earlier than effective US filing date and any foreign priority date) 2002.

Cuoco, Jr., Frank A. et al. Measurement of External Pressures Generated by Nerve Cuff Electrodes. IEEE Transactions on Rehabilitation Engineering. 8 (1): 35-41. Mar. 2000.
Cyberonics, Inc. Equity Research dated Jan. 16, 2003 by Pacific Growth Equities pp. 1-14.
Denny, N.M. et al. Evaluation of an Insulated Tuohy Needle System for the Placement of Interscalene Brachial Plex Catheters. Anaesthesia. 58 (6): 554-7. (Abstract Only). Jun. 2003.
Dorsal Root Ganglion; www.biology-online.org/dDorsal_root_ganglion; downloaded Nov. 5, 2013; 4 pgs.
Dreyfuss, Paul et al. Efficacy and Validity of Radiofrequency Neurotomy for Chronic Lumbar Zygapophysial Joint Pain. Spine. 25 (10): 1270-1277. May 15, 2000.
Dubuisson, D. Treatment of Occipital Neuralgia by Partial Posterior Rhizotomy at C1-3. J Neurosurg. 82 (4): 581-6. (Abstract Only). Apr. 1995.
Eschenfelder, Sebastian et al. Dorsal Root Section Elicits Signs of Neuropathic Pain Rather than Reversing Them in Rats With L5 Spinal Nerve Injury. Pain. 87 (2): 213-219. Aug. 2000.
Firth, Ava et al. Development of a Scale to Evaluate Postoperative Pain in Dogs. J Am Vet Med Assoc. 214 (5): 651-659. Mar. 1, 1999.
Garcia Cosamalon, P.J. et al. Dorsal Percutaneo Radiofrequency Rhizotomy Guided With CT Scan in Intercostal Neuralgias. Technical note. Acta Neurochir (Wien). 109(3-4): 140-1. (year of pub. Sufficiently earlier than effective US filing date and any foreign priority date) 1991.
Giorgi, C. et al. Surgical Treatment of Glossopharyngeal Neuralgia and Pain From Cancer of the Nasopharynx. A 20-Year Experience. J Neurosurg. 61 (5): 952-5. (Abs. Only). Nov. 1984.
Gocer, A.I. et al. Percutaneous Radiofrequency Rhizotomy of Lumbar Spinal Facets the Results of 46 cases. Neurosurg Rev. 20 (2): 114-6. (Abstract Only). (year of pub. sufficiently earlier than effective US filing date and any foreign priority date) 1997.
Haller, H. et al. Treatment of Chronic Neuropathic Pain After Traumatic Central Cervical Cord Lesion with Gabapentin. Journal of Neural Transmission. 110 (9): 977-981. Sep. 2003.
Herron, L.D. Selective Nerve Root Block in Patient Selection for Lumbar Surgery: Surgical Results. J Spinal Disord. 2 (2): 75-9. (Abstract Only). Jun. 1989.
Higuchi, Yoshinori, et al. Exposure of the Dorsal Root Ganglion in Rats to Pulsed Radiofrequency Currents Activates Dorsal Horn Lamina I and II Neurons. Neurosurgery. 50 (4): 850-856. Apr. 2002.
Holsheimer, J. et al. Effects of Electrode Geometry and Combination on Nerve Fibre Selectivity in Spinal Cord Stimulation. Medical & Biological Engineering & Computing. 33 (5): 676-682. Sep. 1995.
Horsch, S. et al. Epidural spinal cord stimulation in the treatment of severe peripheral arterial occlusive disease; Annals of Vascular Surgery; 8(5): 468-74. Sep. 1994.
Igarashi, T. et al. Lysis of Adhesions and Epidural Injection of Steroid/Local Anaesthetic During Epiduroscopy Potentially Alleviate Low Back and Leg Pain in Elderly Patients With Lumbar Spinal Stenosis. British Journal of Anaesthesia. 93 (2): 181-7.Aug. 2004.
Julius, David et al. Molecular Mechanisms of Nociception. Nature. 413 (6852): 203-210. Sep. 13, 2001.
Kanpolat, Yucel et al. Percutaneo Controlled Radiofrequency Trigeminal Rhizotomy for the Treatment of Idiopathic Trigeminal Neuralgia: 25-Year Experience with 1600 Patients. Neurosurgery. 48 (3): 524-534. Mar. 2001.
Kapadia, N.P. et al. Gabapentin for Chronic Pain in Spinal Cord Injury: A Case Report. Arch Phys Med Rehabil. 81 (10): 1439-41. (Abstract Only). Oct. 2000.
Kapoor, Vibhu et al. Refractory Occipital Neuralgia: Preoperative Assessment With CT-Guided Nerve Block Prior to Dorsal Cervical Rhizotomy. American Journal of Neuroradiology. 24 (10): 2105-10. Nov.-Dec. 2003.
Karai, Laszlo et al. Deletion of Vanilloid Receptor 1-Expressing Primary Afferent Neurons for Pain Control. Journal of Clinical Investigation. 113 (9): 1344-1352. May 2004.
Kline, David G. et al. Management and Results of Sciatic Nerve Injuries: a 24-Year Experience. Journal of Neurosurgery. 89 (1): 13-23. Jul. 1998.

(56) References Cited

OTHER PUBLICATIONS

Kobayashi, Shigeru et al. Pathology of Lumbar Nerve Root Compression Part 1: Intraradicular Inflammatory Changes Induced by Mechanical Compression. Journal of Orthopaedic Research. 22 (1): 170-179. Jan. 2004.

Kobayashi, Shigeru et al. Pathology of Lumbar Nerve Root Compression Part 2: Morphological and Immunohistochemical Changes of Dorsal Root Ganglion. Journal of Orthopaedic Research. 22 (1): 180-188. Jan. 2004.

Kocsis et al.; NR2B receptors are involved in the mediation of spinal segmental reflex potentials but not in the cumulative motoneuronal depolarization in vitro; Brain Research Bulletin, Elsevier Science Ltd.; vol. 64; No. 2; pp. 133-138; Aug. 30, 2004.

Koszewski, W. et al. [The DREZ Lesion as an Effective Treatment for Chronic Hypothetically Post-Herpetic Neuropathic Pain. Case Report and Review of Literature]. Neurol Neurochir Pol. 37 (4): 943-53. (Abstract Only). (year of pub. sufficiently earlier than effective US filing date and any foreign priority date) 2003.

Lawrence, Stephen M. et al. Long-Term Biocompatibility of Implanted Polymer-Based Intrafascicular Electrodes. Journal of Biomedical Materials Research. Article first publ. online: 63 (5): 501-506. Jul. 31, 2002.

Lee, In-Seop et al. Characterization of Iridium Film as a Stimulating Neural Electrode. Biomaterials. 23 (11): 2375-2380. Jun. 2002.

Lew, Henry L. et al. Preganglionic Approach to Transforaminal Epidural Steroid Injections. Am. J. Phys. Med. Rehabil. 83 (5): 378. May 2004.

Lopez et al.; Excitatory and inhibitory effects of serotonin on spinal nociceptive reflexes . . . ; (Database Biosis Biosciences information service, Philadelphia, PA, US, XP002567533, accession No. PREV200100573757); Abstract; (year of pub. sufficiently earlier than effective US filing date and any foreign priority date) 2001.

Ma et al.; Enhanced excitability of dissociated primary sensory neurons after chronic compression of the dorsal root ganglion in the rat; Pain; 113(1-2); pp. 106-112; Jan. 2005.

Maher, C.O. et al. Lateral Exit-Zone Stenosis and Lumbar Radiculopathy. J Neurosurg. 90 (1 Suppl): 52-8. Jan. 1999. (Abstract Only).

Mailley, Sophie et al. Thin Film Platinum Cuff Electrodes for Neurostimulation: In Vitro Approach of Safe Neurostimulation Parameters. Bioelectrochemistry. 63(1-20: 359-364. Jun. 2004.

Masini, Michelle et al. Activated Pyrolytic Carbon Tip Pacing Leads: An Alternative to Steroid-Eluting Pacing Leads? PACE. 19(11 Pt 2): 1832-1835. Nov. 1996.

Mayfield Clinic for Brain & Spine; printed from http://www.mayfieldclinic.com/PE-AnatSpine.htm (last updated Jan. 2013); 7 pages.

Medicinenet.com; Definition of Lateral; printed from http://www.medterms.com/script/main/artasp?articlekey=6226 (on Jun. 4, 2014); 3 pages.

Medtronic, Inc. Equity Research dated Dec. 18, 2002 by Pacific Growth Equities pp. 1-20.

Medtronic. Analysis of Sales/Earnings-F1Q05: Many Gives and Takes in the Quarter dated Aug. 20, 2004 by Morgan Stanley pp. 1-25.

Methods of Placement of Neurostimulation Lead, Infusion, Catheter, and/or Sensor Via Peripheral Vasculature. From IP.com PriorArtDatabase—Apr. 10, 2003—#000012136 http://www.priorartdatabase.com/IPCOM/000012136.

Bernstein et al. A Prospective Clinical Evaluation of a Rechargeable IPG: An Interim Analysis of Sustainability of Treatment; (Presentation Abstract): North American Neuromodulation Society; Abs. No. 2010-A-132-NANS; p. 126; Las Vegas, NV.; Dec. 2-5, 2010.

Modern Ideas: The Gate Control Theory of Chronic Pain. Spine-Health.com: Your Comprehensive Resource for Back Pain. http://www.spine-health.com/topics/cd/pain/chronic_pain_theories/chronic_pain_theory02.html (accessed Feb. 24, 2006); 2 pages.

Mond, Harry G. et al. Implantable Transveno Pacing Leads: The Shape of Things to Come. PACE. 27: 887-893. Jun. 2004.

Monti, Enrico. Peripheral Nerve Stimulation: A Percutaneous Minimally Invasive Approach. Neuromodulation. 7 (3): 193. Jul. 2004. (Abstract Only).

Myles et al.; Effects of different methods of peripheral nerve repair on the number and distribution of muscle afferent neurons in rat dorsal root ganglion; J Neurosurg; 77(3); pp. 457-462; Sep. 1992.

Nannini et al.; Muscle recruitment with intrafascicular electrodes; IEEE Trans on Biomedical Engineering; vol. 38; No. 8; pp. 769-776; Aug. 1991.

Naples, Gregory G. A Spiral Nerve Cuff Electrode for Peripheral Nerve Stimulation. IEEE Transactions on Biomedical Engineering. 35 (11): 905-916. Nov. 1988.

Narozny, Martin et al. Therapeutic Efficacy of Selective Nerve Root Blocks in the Treatment of Lumbar Radicular Leg Pain. Swiss Med Wkly. 131(5-6): 75-80. Feb. 2001.

Nashold, Blaine S. et al. Peripheral Nerve Stimulation for Pain Relief Using a Multicontact Electrode System. Technical note. Journal of Neurosurgery. 51 (6): 872-873. Dec. 1979.

Nashold, Blaine S. et al. Long-Term Pain Control by Direct Peripheral-Nerve Stimulation. The Journal of Bone and Joint Surgery. 64 (1): 1-10. Jan. 1982.

Neumann, Simona et al. Regeneration of Sensory Axons Within the Injured Spinal Cord Induced by Intraganglionic cAMP Elevation. Neuron. 34 (6): 885-93. Jun. 13, 2002.

Nielson, K.D. et al. Peripheral Nerve Injury From Implantation of Chronic Stimulating Electrodes for Pain Control. Surg Neurol. 5 (1): 51-3. (Abstract Only).Jan. 1976.

North, Richard B. et al. Dorsal Root Ganglionectomy for Failed Back Surgery Syndrome: A 5-Year Follow-Up Study. J Neurosurg. 74(2): 236-242. Feb. 1991.

North, Richard B. et al. Chapter 123: Current Concepts in the Neurosurgical Management of Persistent Pain (pp. 1634-1637). Operative Neurosurgical Techniques 4th Edition (Henry H. Schmidek et al. eds.). Philadelphia: W.B. Saunders Company, Publ. date Aug. 18, 2000.

Nygaard, Oystein P. et al. The Function of Sensory Nerve Fibers in Lumbar Radiculopathy: Use of Quantitative Sensory Testing in the Exploration of Different Populations of Nerve Fibers and Dermatomes. Spine. 23 (3): 348-352. Feb. 1, 1998.

Obata, K. et al. Activation of Extracellular Signal-Regulated Protein Kinase in the Dorsal Root Ganglion Following Inflammation Near the Nerve Cell Body. Neuroscience. 126 (4): 1011-1021. Accepted Apr. 22, 2004.

Obata, Koichi, et al. Expression of Neurotrophic Factors in the Dorsal Root Ganglion in a Rat Model of Lumbar Disc Herniation. Pain. 99 (1-2): 121-132. Sep. 2002.

Olby, Natasha J. et al. Development of a Functional Scoring System in Dogs With Acute Spinal Cord Injuries. Am J Vet Res. 62(10): 1624-1628. Oct. 2001.

Parlier-Cuau, Caroline et al. Symptomatic Lumbar Facet Joint Synovial Cysts: Clinical Assessment of Facet Joint Steroid Injection After 1 and 6 Months and Long-Term Follow-Up in 30 Patients. Radiology. 210 (2): 509-513. Feb. 1999.

Pedrolli, C. et al. [Dorsolumbar Arachnoid Cysts. A Case Report]. Recenti Prog Med. 81 (11): 699-701. Nov. 1990. (Abstract Only).

The Peripheral Nervous System; http://cnx.org/content/m44751/latest; downloaded Nov. 5, 2013; 7 pgs.

Prats-Galino et al.; Representations of hindlimb digits in rat dorsal root ganglia; J Comp Neurol; 408(1); pp. 137-145; May 24, 1999.

Rodriguez, Francisco J. et al. Polyimide Cuff Electrodes for Peripheral Nerve Stimulation. Journal of Neuroscience Methods. 98 (2): 105-118. Jun. 1, 2000.

Rokugo, Tomoyuki et al. A Histochemical Study of Substance P in the Rat Spinal Cord: Effect of Transcutaneo Electrical Nerve Stimulation. J Nippon Med Sch. 69 (5): 428-433. Oct. 2002.

Romero, E. et al. Neural Morphological Effects of Long-Term Implantation of the Self-Sizing Spiral Cuff Nerve Electrode. Medical & Biological Engineering & Computing. 39 (1): 90-100. Jan. 2001.

Rongstad, K. et al. Popliteal Sciatic Nerve Block for Postoperative Analgesia. Foot Ankle Int. 17 (7): 378-82. Jul. 1996. (Abstract Only).

(56) References Cited

OTHER PUBLICATIONS

Ruetten, S. et al. Endoscopic Surgery of the Lumbar Epidural Space (Epiduroscopy): Results of Therapeutic Intervention in 93 Patients. Minim Invasive Neurosurg. 46 (1): 1-4. Feb. 2003. (Abstract Only).
Sairyo, K. et al. A New Endoscopic Technique to Decompress Lumbar Nerve Roots Affected by Spondylolysis. Technical Note. J Neurosurg. 98(3): 290-3. Apr. 2003. (Abstract Only).
Salame, K. et al. Surgical Treatment of Spasticity by Selective Posterior Rhizotomy 30 Years Experience. Isr Med Assoc J. 5 (8): 543-6. Aug. 2003. (Abstract Only).
Saris, S.C. et al. Sacrococcygeal Rhizotomy for Perineal Pain. Neurosurgery. 19 (5): 789-93. Nov. 1986. (Abstract Only).
Sauvage, P.J. et al. Intraspinal Synovial Cysts of the Lumbar Spine: Imaging Findings and Treatment; [Kystes Synoviaux Intraspinaux Lombaires: Imagerie et Traitement Par Infiltration. A Propos De. (year of pub. sufficiently earlier than effective US filing date and any foreign priority date) 2000.
Schwartzman, Robert J. et al. Neuropathic Central Pain: Epidemiology, Etiology, and Treatment Options. Arch Neurol. 58 (10): 1547-1550. Oct. 2001.
Sedan, R. et al. Therapeutic Electrical Neurostimulation. French Language Society of Neurosurgery—28th Annual Congress—Athens, May 29-30, 1978. Neurochirurgie. 24: 3-& Suppl. 1 (in French with English Summary pp. 121-125).
Sheth, Rishi N. et al. Mechanical Hyperalgesia After an L5 Ventral Rhizotomy or an L5 Ganglionectomy in the Rat. Pain. 96: 63-72. Mar. 2002.
Siddall, Philip J. et al. Persistent Pain as a Disease Entity: Implications for Clinical Management. Anesth Analg. 99: 510-20. Aug. 2004.
Silvers, H.R. Lumbar Percutaneo Facet Rhizotomy. Spine. 15 (1): 36-40. Jan. 1990. (Abstract Only).
Slappendel, R. et al. The efficacy of Radiofrequency Lesioning of the Cervical Spinal Dorsal Root Ganglion in a Double Blinded Randomized Study: No difference Between 40 Degrees C and 67 Degrees C Treatments. Pain. 73 (2): 159-63. Nov. 1997. (Abstract Only).
Sluijter, Menno E. et al. The Effects of Pulsed Radiofrequency Fields Applied to the Dorsal Root Ganglion—A Preliminary Report. The Pain Clinic. 11 (2): 109-117. (year of pub. sufficiently earlier than effective US filing and any foreign priority date) 1998.
Smith, H.P. et al. Radiofrequency Neurolysis in a Clinical Model: Neuropathological Correlation. J Neurosurg. 55 (2): 246-53. Aug. 1981. (Abstract Only).
Spaic, M. et al. Drez Surgery on Con Medullaris (After Failed Implantation of Vascular Omental Graft) for Treating Chronic Pain ; Acta Neurochir(Wein). 141(12): 1309-1312. (year of pub. sufficiently earlier than effective US filing date and any foreign priority date) 1999.
Spaic, M. et al. Microsurgical DREZotomy for Pain of Spinal Cord and Cauda Equina Injury Origin: Clinical Characteristics of Pain and Implications for Surgery in a Series of 26 Patients. Acta Neurochir (Wien). 144 (5): 453-462. May 2002.
Stanton-Hicks, M. et al. Stimulation of the Central and Peripheral Nervo System for the Control of Pain. Journal of Clinical Neurophysiology. 14 (1): 46-62. Jan. 1997.
Steinbok, P. et al. Complications After Selective Posterior Rhizotomy for Spasticity in Children With Cerebral Palsy. Pediatr Neurosurg. 28 (6): 300-13. Jun. 1998. (Abstract Only).
Stolker, Robert J. et al. The Treatment of Chronic Thoracic Segmental Pain by Radiofrequency Percutaneo Partial Rhizotomy. J Neurosurg. 80(6): 986-992. Jun. 1994.
Strait, T.A. et al. Intraspinal Extradural Sensory Rhizotomy in Patients With Failure of Lumbar Disc Surgery. J Neurosurg. 54(2): 193-6. Feb. 1981. (Abstract Only).
Taha, J.M. et al. Long-Term Results of Radiofrequency Rhizotomy in the Treatment of Cluster Headache. Headache. 35 (4): 193-6. Apr. 1995. (Abstract Only).
Taub, Arthur et al. Dorsal Root Ganglionectomy for Intractable Monoradicular Sciatica: A Series of 61 Patients. Stereotact Funct Neurosurg. 65 (1-4): 106-110. (year of pub. sufficiently earlier than effective US filing date and any foreign priority date) 1995.
Truijen et al.; Parasympathetic control of blood flow to the activated human brain; Exp Physiol; 95(10):980-981; Oct. 2010.
Uematsu, Sumio. Chapter 106: Percutaneo Electrothermocoagulation of Spinal Nerve Trunk, Ganglion, and Rootlets (pp. 1207-1221). Operative Neurosurgical Techniques, Indications, Methods and Results 2nd edition. (Henry H. Schmidek et al. eds.). (year of pub. sufficiently earlier than effective US filing date and any foreign priority date) 1988.
Van Zundert, Jan et al. Pulsed Radiofrequency in Chronic Pain Management: Looking for the Best Use of Electrical Current. World Institute of Pain. 5 (2): 74-76. Jun. 2005.
Van De Kraats, Everine B. et al. Noninvasive Magnetic Resonance to Three-Dimensional Rotational X-Ray Registration of Vertebral Bodies for Image-Guided Spine Surgery. Spine. 29 (3): 293-297. Feb. 2004.
Van Kleef, M. et al. Effects and Side Effects of a Percutaneo Thermal Lesion of the Dorsal Root Ganglion in Patients with Cervical Pain Syndrome. Pain. 52 (1): 49-53. Jan. 1993.
Van Kleef, M. et al. Radiofrequency Lesion Adjacent to the Dorsal Root Ganglion for Cervicobrachial Pain: A Prospective Double Blind Randomized Study. Neurosurgery. 38 (6): 1127-31. Jun. 1996.
Van Kleef, Maarten et al. Chapter 160: Radiofrequency Lesions in the Treatment of Pain of Spinal Origin (pp. 1585-1599). Textbook of Stereotactic and Functional Neurosurgery 1st Edition. (Philip L. Gildenberg et al. eds.). New York: McGraw-Hill. (year of pub. sufficiently earlier than effective US filing date and any foreign priority date) 1998.
Van Zundert, J. et al. Pulsed and Continuous Radiofrequency Current Adjacent to the Cervical Dorsal Root Ganglion of the Rat Induces Late Cellular Activity in the Dorsal Horn. Anesthesiology. 102 (1): 125-31. Jan. 2005.
Vaughan, R. Percutaneous Radiofrequency Gangliotomy in the Treatment of Trigeminal Neuralgia and Other Facial Pain. Aust N Z J Surg. 45 (2): 203-7. May 1975. (Abstract Only).
Viton, J.-M. et al. Short-Term Assessment of Periradicular Corticosteroid Injections in Lumbar Radiculopathy Associated With Disc Pathology. Neuroradiology. 40 (1): 59-62. Jan. 1998.
Viton, J.M. et al. Short-Term Evaluation of Periradicular Corticosteroid Injections in the Treatment of Lumbar Radiculopathy Associated With Disc Disease. Rev Rhum Engl Ed. 65 (3): 195-200. Mar. 1998. (Abstract Only).
Wagner, A.L. et al. Selective Nerve Root Blocks. Tech Vasc Intery Radiol. 5(4): 194-200. Dec. 2002. (Abstract Only).
Waxman et al.; Sodium channels, excitability of primary sensory neurons, and the molecular basis of pain; Muscle Nerve; 22(9); pp. 1177-1187; Sep. 1999.
Weiner, Richard L. The Future of Peripheral Nerve Neurostimulation. Neurological Research. 22 (3): 299-304. Apr. 2000.
Weiner, Richard L. Peripheral Nerve Neurostimulation. Neurosurgery Clinics of North America. 14 (3): 401-408. Jul. 2003.
Weinstein, James et al. The Pain of Discography. Spine. 13(12):1344-8. Dec. 1988.
Wedley et al. Handbook of Clinical Techniques in the Management of Chronic Pain. Taylor & Francis; pp. 17-19. Nov. 27, 1996.
Wessels et al.; A rostrocaudal somatotopic organization in the brachial dorsal root ganglia of neonatal rats; Clin Neurol Neurosurg; 95 Suppl; pp. S3-11; (year of pub. sufficiently earlier than effective US filing date and any foreign priority date) 1993.
Wessels et al.; Evidence for a rostrocaudal organization in dorsal root ganglia during development as demonstrated by intra-uterine WGA-HRP injections into the hindlimb of rat fetuses; Brain Res Dev Brain Res; 54(2); pp. 273-281; Jul. 1, 1990.
Wessels et al.; Somatotopic organization in the sensory innervation of the rat hindlimb during development . . . ; Eur J Morphol; 28(2-4); pp. 394-403; (year of pub. sufficiently earlier than effective US filing date and any foreign priority date) 1990.
Wessels et al.; The rostrocaudal organization in the dorsal root ganglia of the rat: a consequence of plexus formation?; Anat Embryol (Berl); 190(1); pp. 1-11; Jul. 1994.

(56) References Cited

OTHER PUBLICATIONS

Wetzel, F. Todd et al. Extradural Sensory Rhizotomy in the Management of Chronic Lumbar Radiculopathy: A Minimum 2-Year Follow-up Study. Spine. 22 (19): 2283-2291. Oct. 1, 1997.
Wetzel, F.T. Chronic Benign Cervical Pain Syndromes: Surgical Considerations. Spine. 17 (10 Suppl): S367-74. Oct. 1992. (Abstract Only).
Wetzel, F.T. et al. The Treatment of Chronic Extremity Pain in Failed Lumbar Surgery. The Role of Lumbar Sympathectomy. Spine. 17 (12): 2367-8. Dec. 1992. (Abstract Only).
White, P.F. et al. The Use of a Continuous Popliteal Sciatic Nerve Block After Surgery Involving the Foot and Ankle: Does It Improve the Quality of Recovery? Anesth Analg. 97 (5): 1303-9. Nov. 2003. (Abstract Only).
Whitworth, Louis Anthony et al. Application of Spinal Ablative Techniques for the Treatment of Benign Chronic Painful Conditions. Spine. 27 (22): 2607-2612. Nov. 15, 2002.
Wilkinson, H.A. et al. Sensory Ganglionectomy: Theory, Technical Aspects, and Clinical Experience. J Neurosurg. 95(1): 61-6. Jul. 2001. (Abstract Only).
Wong, C.B. et al. Clinical Outcomes of Revision Lumbar Spinal Surgery: 124 Patient With a Minimum of Two Years of Follow-Up. Chang Gung Med J. 25 (3): 175-82. Mar. 2002. (Abstract Only).
Wright, Robert E. et al. Neurostimulation of the L2 Dorsal Root Ganglion for Intractable Disc Pain: Description of a Novel Technique. Presented at the IFESS. (year of pub. sufficiently earlier than effective US filing date and any foreign priority date) 1998.
Wu, Gang et al. Early Onset of Spontaneous Activity in Uninjured C-Fiber Nociceptors After Injury to Neighboring Nerve Fibers. Journal of Neuroscience. 21 (8): RC140. Apr. 15, 2001.
Yamashita, Toshihiko et al. A Quantitative Analysis of Sensory Function in Lumbar Radiculopathy Using Current Perception Threshold Testing. Spine. 27 (14): 1567-1570. Jul. 15, 2002.
Yoshida, Hirotoshi et al. Lumbar Nerve Root Compression Caused by Lumbar Intraspinal Gas: Report of Three Cases. Spine. Feb. 1, 1997, vol. 22 (3): 348-351.
Young, R.F. Chapter 161: Dorsal Rhizotomy and Dorsal Root Ganglionectomy (pp. 3442-3451). Neurological Surgery 4th Edition. Jan. 15, 1996. (Julian R. Youmans ed.). Philadelphia: W.B. Saunders Company.
Kishawi et al.; U.S. Appl. No. 13/753,326 entitled "Pain management with stimulation subthreshold to parasthesia," filed Jan. 29, 2013.
Imran; U.S. Appl. No. 14/814,343 entitled "Grouped leads for spinal stimulation," filed Jul. 30, 2015.

* cited by examiner

SELECTIVE STIMULATION TO MODULATE THE SYMPATHETIC NERVOUS SYSTEM

CROSS-REFERENCES TO RELATED APPLICATIONS

This application is a continuation of U.S. patent application Ser. No. 13/458,697, entitled "Selective Stimulation to Modulate the Sympathetic Nervous System", filed on Apr. 27, 2012 which claims priority under 35 U.S.C. 119(e) to U.S. Provisional Patent Application No. 61/480,958, entitled "Selective Stimulation of Dorsal Root Ganglion to Modulate the Sympathetic Nervous System", filed on Apr. 29, 2011, which is incorporated by reference in its entirety. U.S. patent application Ser. No. 13/458,697 is also a continuation-in-part of U.S. patent application Ser. No. 12/369,706, entitled "Methods of Stimulating a Dorsal Root Ganglion", filed on Feb. 11, 2009, now U.S. Pat. No. 8,229,565, which is a divisional of U.S. patent application Ser. No. 11/222,516, entitled "Methods for Stimulating a Dorsal Root Ganglion", filed on Sep. 7, 2005, now U.S. Pat. No. 7,502,651, which claims priority under 35 U.S.C. 119(e) to U.S. Provisional Patent Application No. 60/608,357, entitled "Neurostimulation Systems and Methods", filed on Sep. 8, 2004, all of which are incorporated herein by reference in their entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND

A variety of diseases and medical conditions plague the population causing pain, dysfunction, distress, social problems, and ultimately death. These may be caused by external factors, such as infectious disease, or caused by internal dysfunctions, such as autoimmune diseases. Such conditions usually affect people not only physically but also emotionally.

Consequently, a vast array of medical treatments and therapies have been generated in an attempt to prevent, improve, palliatively treat or cure these medical conditions. Examples of such treatments have included the development of drugs, medical devices, gene therapy, hormone therapy, biotherapy, virotherapy, bacteriophage therapy, ozonotherapy, hydrotherapy, neuromodulation, phototherapy, and radiation, to name a few.

However, many of these treatments cause adverse effects in addition to or in place of the intended therapeutic effect. Common adverse effects include alteration in body weight, change in enzyme levels, loss of function, development of pain, or pathological changes detected at the microscopic, macroscopic or physiological level, to name a few. The severity of adverse effects can range from nausea to death.

Therefore, there remains a need for the further development of devices, systems and methods of treating various medical conditions while reducing or eliminating adverse effects. Such devices, systems and methods should be targeted with minimal deleterious effects on unaffected body regions. At least some of these objectives will be met by the present invention.

SUMMARY OF THE DISCLOSURE

The present invention provides targeted treatment of a variety of medical conditions by directly neuromodulating a target anatomy associated with the condition while minimizing or excluding undesired neuromodulation of other anatomies. In preferred embodiments, the target anatomy includes one or more dorsal root ganglia, dorsal roots, dorsal root entry zones, or portions thereof. Such target stimulation areas are utilized due in part to their effect on the sympathetic nervous system. In particular, many of these target anatomies house sensory fibers that are isolated from motor fibers. Sensory fibers are involved in a variety of reflexes and feed-forward physiologic processes that control the sympathetic nervous system and these reflexes and processes can be utilized in the treatment of various disorders. In addition, in some embodiments, such targeted neuromodulation reduces or eliminates undesired side effects, such as painful tingling or unwanted movements caused by direct stimulation of motor nerves, such as within the ventral root. Further, such targeted therapy minimizes or eliminates global activation or inactivation of the sympathetic nervous system and the complications that arise from such activation or inactivation.

In a first aspect of the present invention, a method is provided of modulating a neural pathway in the sympathetic nervous system. In some embodiments, the method comprises positioning at least one electrode of a lead in close proximity to a dorsal root ganglion upstream of at least one ganglion of the sympathetic nerve chain, and providing energy to the at least one electrode so as to neuromodulate the dorsal root ganglion in a manner that influences a condition associated with the at least one ganglion of the sympathetic nerve chain while excluding neuromodulation of an associated ventral root.

In some embodiments, neuromodulating a dorsal root ganglion comprises neuromodulating a dorsal root ganglion in a manner that influences functional activation of a bodily system associated with the at least one ganglion along the sympathetic nerve chain. In other embodiments, the neuromodulating a dorsal root ganglion comprises neuromodulating a dorsal root ganglion in a manner that influences functional activation of an organ associated with the at least one ganglion along the sympathetic nerve chain.

In some embodiments, neuromodulating a dorsal root ganglion comprises neuromodulating a dorsal root ganglion in a manner that influences functional inhibition of a bodily system associated with the at least one ganglion along the sympathetic nerve chain. Further, in some embodiments, neuromodulating a dorsal root ganglion comprises neuromodulating a dorsal root ganglion in a manner that influences functional inhibition of an organ associated with the at least one ganglion along the sympathetic nerve chain.

In some embodiments, neuromodulating a dorsal root ganglion comprises neuromodulating a dorsal root ganglion in a manner that lessens vascular resistance of a blood vessel associated with the at least one ganglion along the sympathetic nerve chain. In other embodiments, neuromodulating a dorsal root ganglion comprises neuromodulating a dorsal root ganglion in a manner that improves vascular perfusion to an ischemic body region or tissue.

It may be appreciated that in some embodiments the condition comprises an ischemic disorder, diabetes, peripheral vascular disease, stroke, erectile dysfunction, a sympathetically maintained or mediate pain condition, Raynaud's disease, heart disease, angina pectoris, vascular disease, a skin ulceration, a wound healing disorder, asthma, hypertension, an immune system disorder or a renal disorder, but is not so limited. It may also be appreciated that in some embodiments the at least one ganglion of the sympathetic nerve chain is a cervical ganglion, a thoracic ganglion or a lumbar ganglion.

In some embodiments, the positioning step comprises positioning the at least one electrode on the dorsal root ganglion epinurium.

In other embodiments, the method further comprises directly applying stimulation to the at least one ganglion along the sympathetic nerve chain. In some instances, the directly applying stimulation step for the at least one ganglion along the sympathetic nerve chain is performed using an electrode exposed to the at least one ganglion along the sympathetic nerve chain.

In a second aspect of the present invention, another method is provided of modulating a portion of a neural pathway in the sympathetic nervous system. In some embodiments, the method includes positioning at least one electrode of a lead in close proximity to a target dorsal root ganglion associated with the portion of the neural pathway, and energizing the at least one electrode so that the portion of the neural pathway is altered and energy provided by the at least one electrode dissipates within the target dorsal root ganglion while excluding an associated ventral root.

In some embodiments, the energy provided by the at least one electrode selectively stimulates a soma and/or one of the ascending or descending axons within the target dorsal root ganglion which activates a premotor neuron. In some instances, the activation of the premotor neuron acts upon a sympathetic motor neuron causing inhibition of the release of norephinephrine by the sympathetic motor neuron. In some instances, the activation of the premotor neuron acts upon a sympathetic motor neuron causing inhibition of vascular resistance in a blood vessel influenced by the sympathetic motor neuron.

In some embodiments, altering of the portion of the neural pathway increases perfusion to a region of the body associated with the portion of the neural pathway. In some instances, the region of the body comprises a brain. In other instances, the region of the body comprises an ischemic limb. In some embodiments, altering of the portion of the neural pathway increases perfusion to a portion of a peripheral vascular system affected by a peripheral vascular disease. And in some embodiments, altering of the portion of the neural pathway alleviates sympathetically mediated pain or sympathetically maintained pain.

Other objects and advantages of the present invention will become apparent from the detailed description to follow, together with the accompanying drawings.

DETAILED DESCRIPTION

Figure 1:
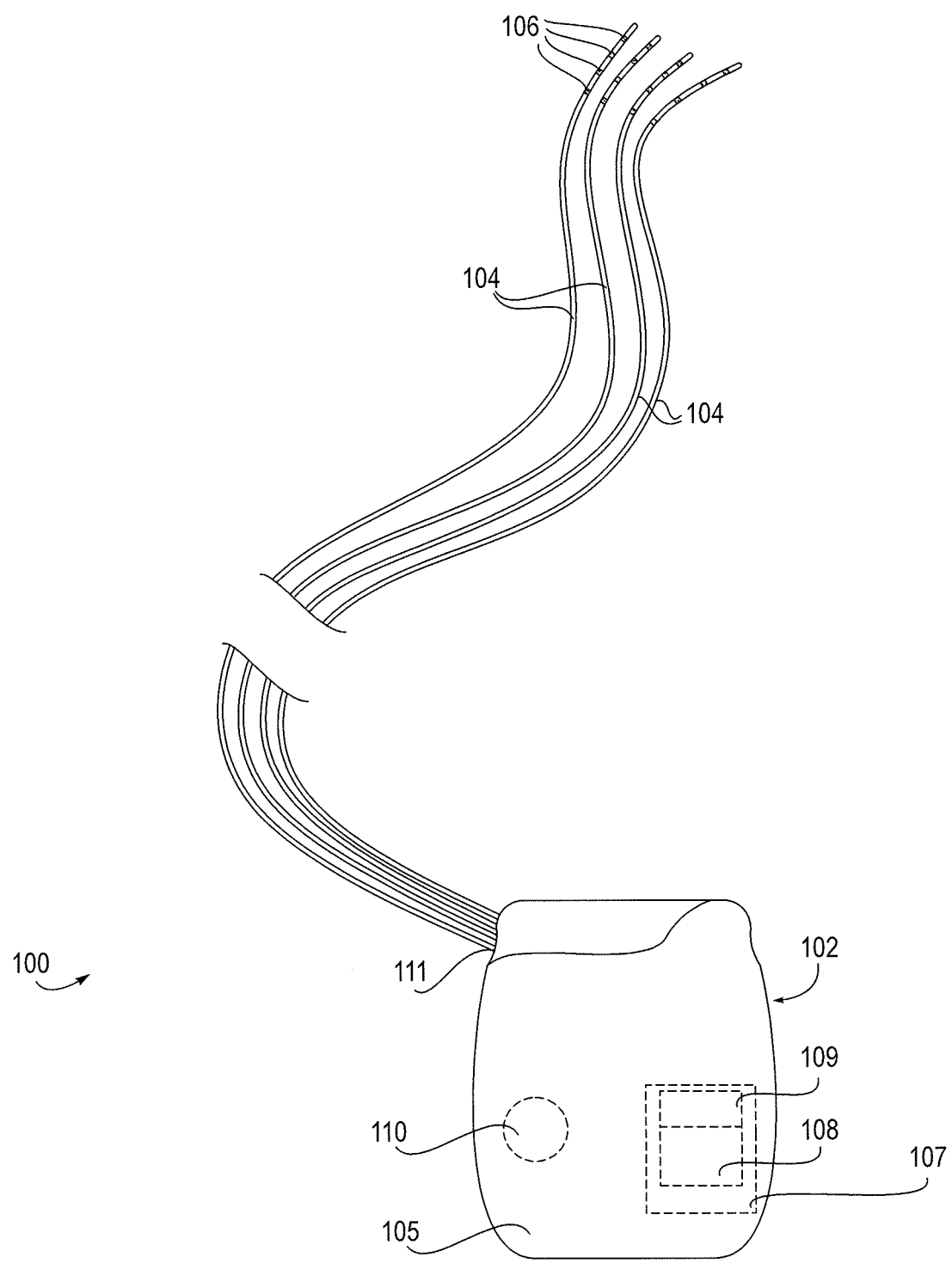
FIG. 1 illustrates an embodiment of an implantable stimulation system.

The sympathetic system is responsible for mobilizing the body's responses under stressful situations, also known as the 'flight or fight' response. The sympathetic system acts on many different organs of the body including the eyes (contraction and dilation of the pupils), heart (increase in heart rate, blood flow, blood pressure), lungs (dilation of bronchioles), digestive system (inhibiting movement of food), kidney (increase secretion of rennin), and penis (promote ejaculation). The sympathetic system is also active at a basal level on these and many organs so as to maintain a state of homeostasis in the body.

Given the unique role of the sympathetic system in the body and the ability of the sympathetic system to affect a wide array of internal organs, the sympathetic system may be utilized to treat a variety of conditions throughout the body. Such conditions include, but are not limited to, ischemic disorders, diabetes, peripheral vascular disease, stroke, erectile dysfunction, sympathetically maintained or mediate pain conditions, Raynaud's disease, heart disease, angina pectoris, vascular disease, skin ulcerations, wound healing disorders, asthma, hypertension, immune system disorders, and renal disorders, to name a few.

Many of these conditions involve ischemia or impaired blood flow to a particular region of the body. Although such impairment of blood flow is caused by a myriad of factors depending on the condition suffered by the patient, increase in blood flow to these areas can assist in treating these conditions and can be achieved by affecting the sympathetic nervous system.

Blood flow and pressure is continuously regulated by nerves. At specific locations in the walls of blood vessels, including the aortic arch and carotid sinus, blood pressure is sensed based on the amount of stretch in the walls. When blood pressure increases for any reason, nerve signals are sent to the blood pressure regulating centers located in the brainstem and suprabulbar regions. In response to the nerve signals, the blood pressure regulating centers send out nerve signals that slow the heart and dilate the blood vessels resulting in lowering of the blood pressure back toward its normal basal level. The basal level can be considered vascular tone. In general, vascular tone refers to the degree of constriction experienced by a blood vessel relative to its maximally dilated state. All arterial and venous vessels under basal conditions exhibit some degree of smooth muscle contraction that determines the diameter, and hence tone, of the vessel. Basal vascular tone differs among organs. Those organs having a large vasodilatory capacity (e.g., myocardium, skeletal muscle, skin, splanchnic circulation) have high vascular tone, whereas organs having relatively low vasodilatory capacity (e.g., cerebral and renal circulations) have low vascular tone.

Vascular tone is determined by many different competing vasoconstrictor and vasodilator influences acting on the blood vessel. These influences can be separated into extrinsic factors that originate from outside of the organ or tissue in which the blood vessel is located, and intrinsic factors that originate from the vessel itself or the surrounding tissue. The primary function of extrinsic factors is to regulate arterial blood pressure by altering systemic vascular resistance, whereas intrinsic mechanisms are important for local blood flow regulation within an organ. Vascular tone at any given time is determined by the balance of competing vasoconstrictor and vasodilator influences.

In general, activation of extrinsic factors and control mechanisms can either increase or decrease vascular tone (i.e., cause vasoconstriction). In one such example, increasing sympathetic nerve activity can increase vascular tone, thus causing an increase in vasoconstriction. Therefore, inhibition of the sympathetic nervous system causes arterial vasodilation and improved blood flow to areas that suffer from restricted blood flow. Thus, treatment of a condition involving ischemia or impaired blood flow to a particular region of the body may be treated by inhibition of portions of the sympathetic nervous system. However, it may be appreciated that in some instances, treatment of a condition (including conditions involving ischemia or impaired blood flow) may be treated by activation of portions of the sympathetic nervous system. The present invention provides for such types of treatment, in addition to other utilizations of the sympathetic nervous system to treat a variety of conditions.

The present invention provides for targeted treatment of such conditions with minimal deleterious side effects, such as undesired motor responses, undesired stimulation of unaffected body regions, global activation or inactivation of the sympathetic nervous system and the complications that arise from such activation or inactivation. This is achieved by directly neuromodulating a target anatomy associated with the condition while minimizing or excluding undesired neuromodulation of other anatomies. In most embodiments, neuromodulation comprises stimulation, however it may be appreciated that neuromodulation may include a variety of forms of altering or modulating nerve activity by delivering electrical or pharmaceutical agents directly to a target area. For illustrative purposes, descriptions herein will be provided in terms of stimulation and stimulation parameters, however, it may be appreciated that such descriptions are not so limited and may include any form of neuromodulation and neuromodulation parameters.

Typically, the systems and devices are used to neuromodulate portions of neural tissue of the central nervous system, wherein the central nervous system includes the spinal cord and the pairs of nerves along the spinal cord which are known as spinal nerves. The spinal nerves include both dorsal and ventral roots which fuse to create a mixed nerve which is part of the peripheral nervous system. At least one dorsal root ganglion (DRG) is disposed along each dorsal root prior to the point of mixing. Thus, the neural tissue of the central nervous system is considered to include the dorsal root ganglions and exclude the portion of the nervous system beyond the dorsal root ganglions, such as the mixed nerves of the peripheral nervous system. Typically, the systems and devices of the present invention are used to selectively stimulate one or more dorsal root ganglia, while minimizing or excluding undesired stimulation of other tissues, such as surrounding or nearby tissues, ventral root and portions of the anatomy associated with body regions which are not targeted for treatment. In other embodiments, dorsal roots, dorsal root entry zones, or portions are targeted for stimulation. It may be appreciated that stimulation of other tissues are contemplated.

The target stimulation areas of the present invention, particularly the dorsal root ganglia, are utilized due in part to their effect on the sympathetic nervous system. It is in these areas that sensory fibers are isolated from motor fibers. Sensory fibers are involved in a variety of reflexes and feed-forward physiologic processes that control the sympathetic nervous system and these reflexes and processes can be utilized in the treatment of various disorders. Thus, by stimulating sensory fibers in these areas, fundamental reflexes and processes can be affected to lessen the symptoms of a variety of disorders. In addition, such targeted stimulation reduces undesired side effects, such as painful tingling or unwanted movements caused by direct stimulation of motor nerves, such as within the ventral root.

The present invention utilizes such reflex arcs and feed-forward processes to treat patients presenting with one or more disorders. FIG. 1 illustrates an embodiment of an implantable stimulation system 100 for treatment of such patients. The system 100 includes an implantable pulse generator (IPG) 102 and at least one lead 104 connectable thereto. In preferred embodiments, the system 100 includes four leads 104, as shown, however any number of leads 104 may be used including one, two, three, four, five, six, seven, eight, up to 58 or more. Each lead 104 includes at least one electrode 106. In preferred embodiments, each lead 104 includes four electrodes 106, as shown, however any number of electrodes 106 may be used including one, two, three, four five, six, seven, eight, nine, ten, eleven, twelve, thirteen, fourteen, fifteen, sixteen or more. Each electrode can be configured as off, anode or cathode. In some embodiments, even though each lead and electrode are independently configurable, at any given time the software ensures only one lead is stimulating at any time. In other embodiments, more than one lead is stimulating at any time, or stimulation by the leads is staggered or overlapping.

Referring again to FIG. 1, the IPG 102 includes electronic circuitry 107 as well as a power supply 110, e.g., a battery, such as a rechargeable or non-rechargeable battery, so that once programmed and turned on, the IPG 102 can operate independently of external hardware. In some embodiments, the electronic circuitry 107 includes a processor 109 and programmable stimulation information in memory 108.

Figure 2:
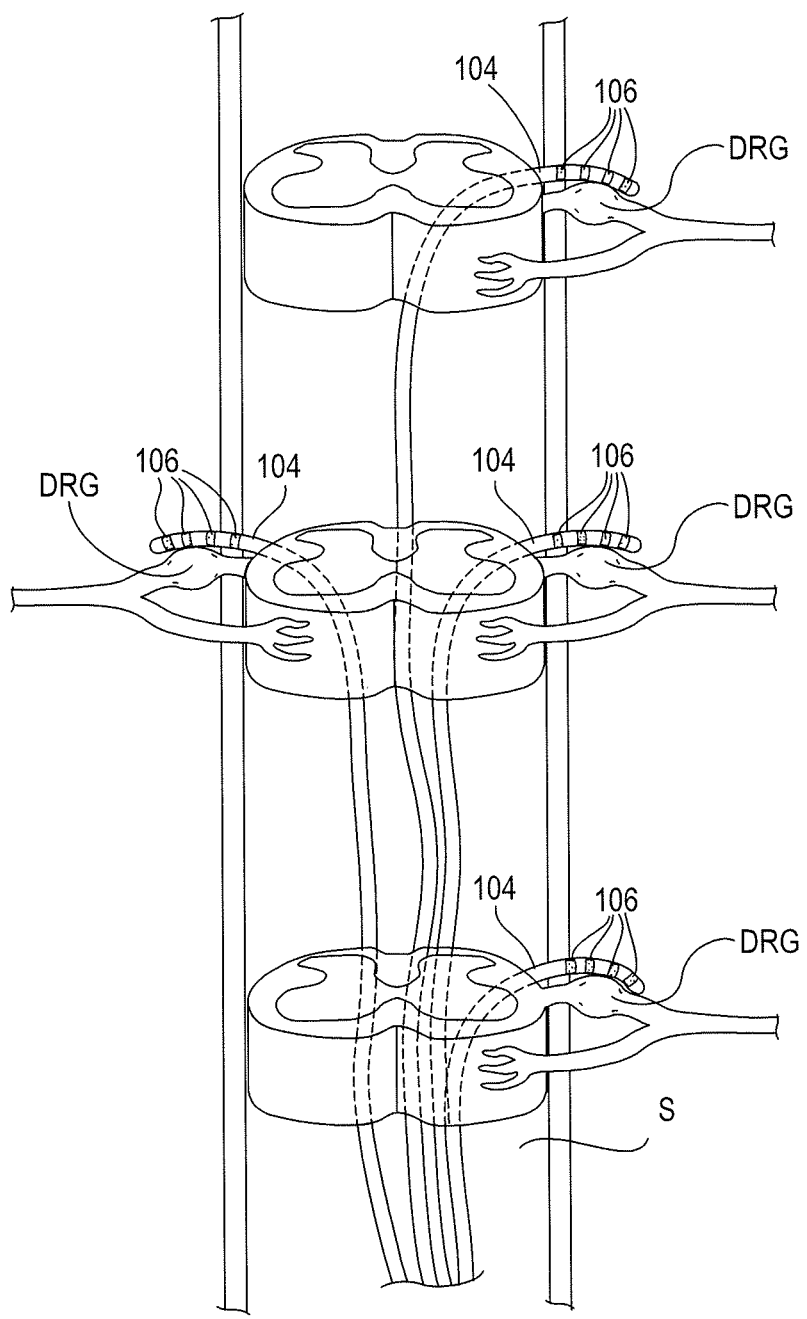
FIG. 2 illustrates example placement of the leads of the embodiment of FIG. 1 within a patient anatomy.

The implantable stimulation system 100 can be used to stimulate a variety of anatomical locations within a patient's body. In preferred embodiments, the system 100 is used to stimulate one or more dorsal roots, particularly one or more dorsal root ganglions. FIG. 2 illustrates example placement of the leads 104 of the embodiment of FIG. 1 within the patient anatomy. In this example, each lead 104 is individually advanced within the spinal column S in an antegrade direction. Each lead 104 has a distal end which is guidable toward a target DRG and positionable so that its electrodes 106 are in proximity to the target DRG. Specifically, each lead 104 is positionable so that its electrodes 106 are able to selectively stimulate the DRG, either due to position, electrode configuration, electrode shape, electric field shape, stimulation signal parameters or a combination of these. FIG. 2 illustrates the stimulation of four DRGs, each DRG stimulated by one lead 104. These four DRGs are located on three levels, wherein two DRGs are stimulated on the same level. It may be appreciated that any number of DRGs and any combination of DRGs may be stimulated with the stimulation system 100 of the present invention. It may also be appreciated that more than one lead 104 may be positioned so as to stimulate an individual DRG and one lead 104 may be positioned so as to stimulate more than one DRG.

It may be appreciated that selective stimulation or neuromodulation concepts described herein may be applied in a number of different configurations. Unilateral (on or in root ganglion(s) on one level on one side of the spinal cord), bi-lateral (on or in two root ganglions on the same level on opposite sides of the spinal cord), unilevel (one or more root ganglion on the same level) or multi-level (at least one root ganglion is stimulated on each of two or more levels) or combinations of the above including stimulation of a portion of the sympathetic nervous system and one or more dorsal root ganglia associated with the neural activity or transmission of that portion of the sympathetic nervous system. As such, embodiments of the present invention may be used to create a wide variety of stimulation control schemes, individually or overlapping, to create and provide zones of treatment.

Figure 3:
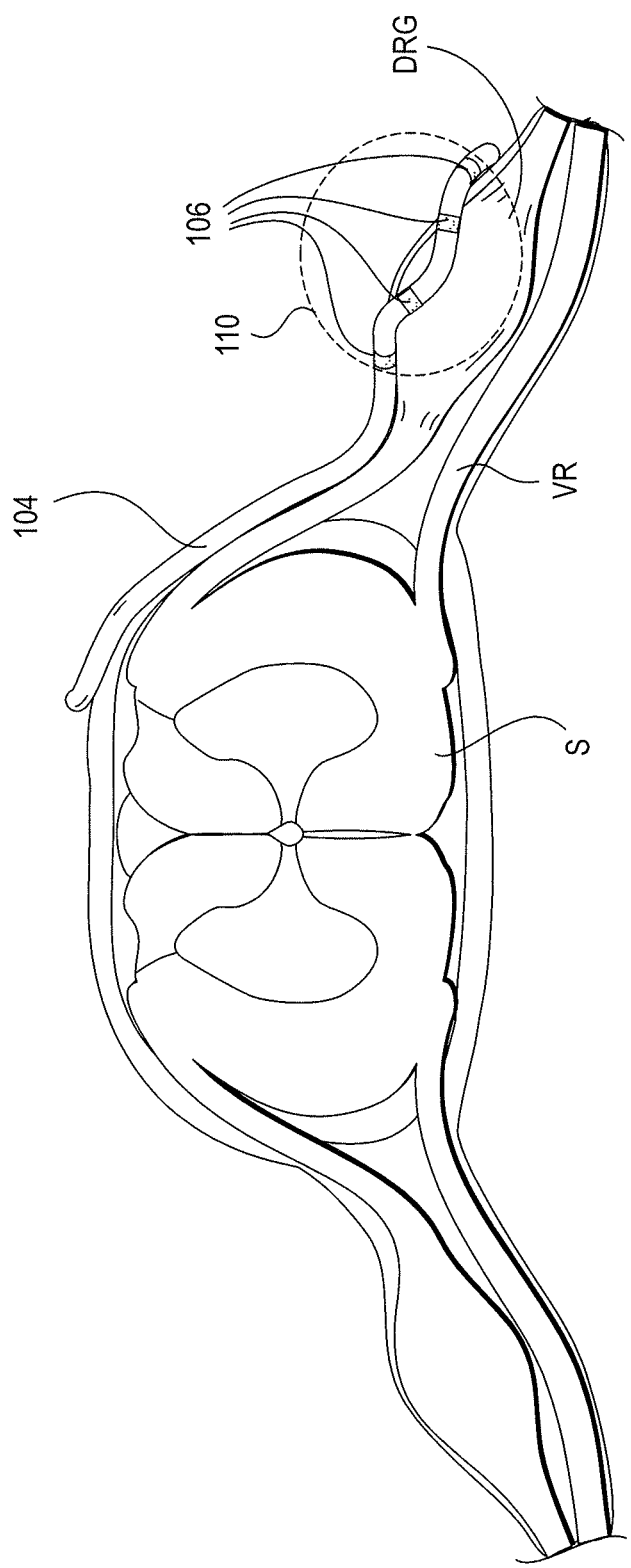
FIG. 3 illustrates an example cross-sectional view of an individual spinal level showing a lead positioned on, near or about a target dorsal root ganglion.

FIG. 3 illustrates an example cross-sectional view of an individual spinal level showing a lead 104 of the stimulation system 100 positioned on a target DRG. In this example, the lead 104 is advanced within the epidural space along the spinal cord S to the appropriate spinal level wherein the lead 104 is advanced laterally toward the target DRG. In some instances, the lead 104 is advanced through or partially through a foramen. At least one, some or all of the electrodes 106 are positioned on, near, about or in proximity to the DRG. In preferred embodiments, the lead 104 is positioned so that the electrodes 106 are disposed along a surface of the DRG opposite to the ventral root VR, as illustrated in FIG. 3. It may be appreciated that the surface of the DRG opposite the ventral root VR may be diametrically opposed to portions of the ventral root VR but is not so limited. Such a surface may reside along a variety of areas of the DRG which are separated from the ventral root VR by a distance.

In some instances, such electrodes 106 may provide a stimulation region indicated by dashed line 110, wherein the DRG receives stimulation energy within the stimulation region and the ventral root VR does not as it is outside of the stimulation region. Thus, such placement of the lead 104 may assist in reducing any possible stimulation of the ventral root VR due to distance. However, it may be appreciated that the electrodes 106 may be positioned in a variety of locations in relation to the DRG and may selectively stimulate the DRG due to factors other than or in addition to distance, such as due to stimulation profile shape and stimulation signal parameters, to name a few. It may also be appreciated that the target DRG may be approached by other methods, such as a retrograde epidural approach. Likewise, the DRG may be approached from outside of the spinal column wherein the lead 104 is advanced extraforaminally, from a outside a foramen toward the spinal column, optionally passing through or partially through a foramen and is implanted so that at least some of the electrodes 106 are positioned on, about or in proximity to the DRG.

In order to position the lead 104 in such close proximity to the DRG, the lead 104 is appropriately sized and configured to maneuver through the anatomy. In some embodiments, such maneuvering includes atraumatic epidural advancement along the spinal cord S, through a sharp curve toward a DRG, and optionally through a foramen wherein the distal end of the lead 104 is configured to then reside in close proximity to a small target such as the DRG. Consequently, the lead 104 is significantly smaller and more easily maneuverable than conventional spinal cord stimulator leads. Example leads and delivery systems for delivering the leads to a target such as the DRG are provided in U.S. patent application Ser. No. 12/687,737, entitled "Stimulation Leads, Delivery Systems and Methods of Use", incorporated herein by reference for all purposes.

Figure 4:
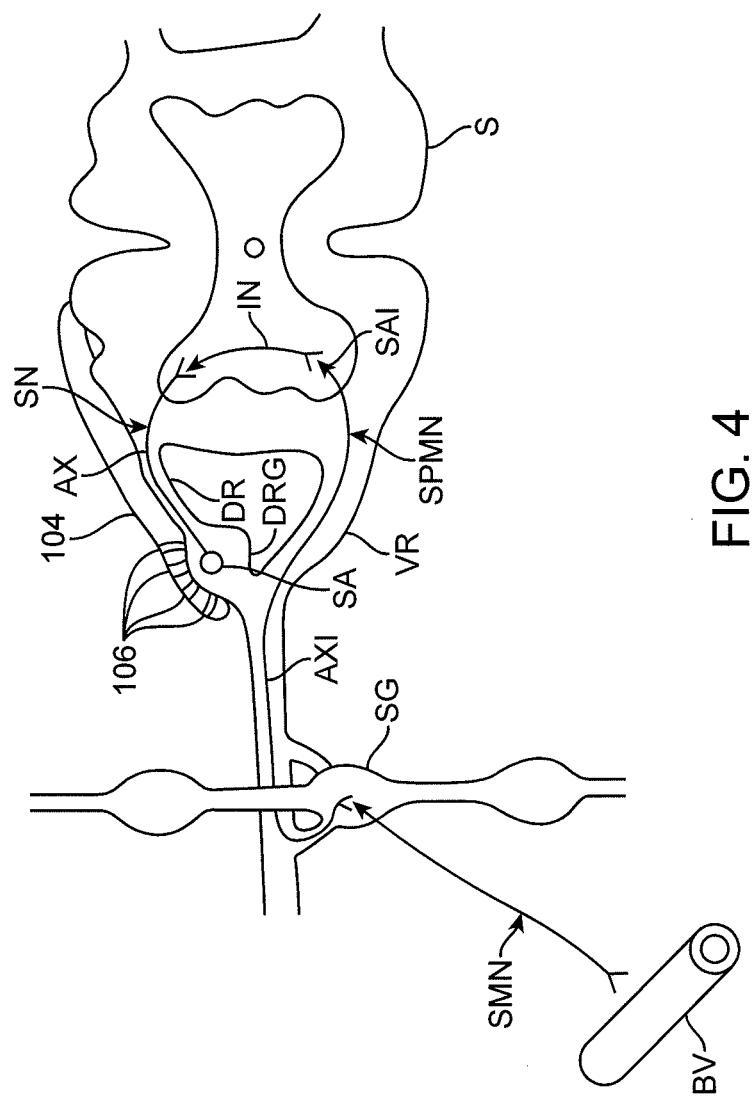
FIG. 4 illustrates a lead positioned near a dorsal root ganglion so as to influence the sympathetic nervous system in the treatment of a condition or disorder.

FIG. 4 illustrates the lead 104 positioned near a DRG so as to influence the sympathetic nervous system in the treatment of a condition or disorder. In this schematic illustration, a sensory neuron SN is shown having a soma SA disposed within the DRG and an axon AX which extends through the dorsal root DR to the dorsal horn of the spinal cord S. The sensory neuron SN connects with an interconnector neuron IN within the spinal cord S which connects with sympathetic premotor neuron SPMN. The sympathetic premotor neuron SPMN includes a soma SA1 disposed within the ventral horn of the spinal cord S and an axon AX1 which extends through the ventral root VR and enervates a sympathetic ganglion SG. Here, the sympathetic premotor neuron SPMN synapses with a sympathetic motor neuron SMN that ultimately affects a blood vessel BV and alters vascular resistance. The sympathetic motor neuron SMN releases norepinephrine, a neurotransmitter. Norepinephrine increases vascular resistance or blood pressure by increasing vascular tone through α-adrenergic receptor activation. It may be appreciated that in other embodiments, the sympathetic motor neuron may release or co-release other transmitters.

As mentioned previously, treatment of a condition involving ischemia or impaired blood flow to a particular region of the body may be treated by inhibition of the sympathetic nervous system. Referring again to FIG. 4, at least one, some or all of the electrodes 106 are positioned on, about or in proximity to the target DRG. In some embodiments, the involved sensory neuron SN, particularly its soma SA within the target DRG, is selectively stimulated by energy provided by at least one of the electrodes 106. Such stimulation is transmitted through the interneuron IN to the sympathetic premotor neuron SPMN which acts upon a sympathetic motor neuron SMN via the associated sympathetic ganglion SG. This inhibits release of norepinephrine by the sympathetic motor neuron SMN which in turn lessens vascular resistance and improves blood flow to the areas that had suffered from restricted blood flow.

In some embodiments, selective stimulation of the involved sensory neuron SN is achieved with the choice of the size of the electrode(s), the shape of the electrode(s), the position of the electrode(s), the stimulation signal, pattern or algorithm, or any combination of these. Such selective stimulation stimulates the targeted neural tissue while excluding untargeted tissue, such as surrounding or nearby tissue. In some embodiments, the stimulation energy is delivered to the targeted neural tissue so that the energy dissipates or attenuates beyond the targeted tissue or region to a level insufficient to stimulate modulate or influence such untargeted tissue. In particular, selective stimulation of tissues, such as the dorsal root, DRG, or portions thereof, exclude stimulation of the ventral root wherein the stimulation signal has an energy below an energy threshold for stimulating a ventral root associated with the target dorsal root while the lead is so positioned. Examples of methods and devices to achieve such selective stimulation of the dorsal root and/or DRG are provided in U.S. patent application Ser. No. 12/607,009, entitled "Selective Stimulation Systems and Signal Parameters for Medical Conditions", incorporated herein by reference for all purposes. It may be appreciated that indiscriminant stimulation of the ventral root, such as from an electrode which emits stimulation energy which directly stimulates the ventral root, typically causes unpleasant sensations for the patient, such as tingling, buzzing or undesired motions or movements. Therefore, it is desired to stimulate sympathetic premotor neurons via synapses in the spinal cord rather than directly via the ventral root.

As mentioned previously, given the unique role of the sympathetic system in the body and the ability of the sympathetic system to affect a wide array of internal organs, the sympathetic system may be utilized to treat a variety of conditions throughout the body. In particular, a condition involving ischemia or impaired blood flow to a particular region of the body may be treated by inhibition or activation of the sympathetic nervous system. Some of these conditions will be described in more detail below. However, it may be appreciated that other disorders and conditions may also be treated with the devices, systems and methods of the present invention.

Diabetes

Diabetes is a metabolism disorder in which the quantity of glucose in the blood is too elevated (hyperglycemia). This is because the body either does not produce enough insulin, produces no insulin, or has cells that do not respond properly to the insulin the pancreas produces. Since insulin makes it possible for cells to take in glucose, this metabolic disorder results in too much glucose building up in the blood.

Elevated blood sugar levels cause a variety of health problems and complications for diabetic patients. A very common complication is foot problems, including nerve damage or peripheral neuropathy that results in loss of feeling or pain and burning sensations in the feet and legs. Once nerve damage progresses, it triggers loss of motor control and abnormal gait and can result in ulcers and amputations. The major cause of such nerve damage is loss of circulation. High blood sugars damage both large and small blood vessels that carry oxygen and nutrients to the nerves. If there is not enough blood being sent to the nerves, the nerves are damaged wherein electrical signals can no longer pass or pass at a slower speed. Good messaging in nerves also depends on an outer protective coating called myelin. This electrical insulator is also vulnerable to damage from high blood sugars. Preventing such foot problems in diabetes begins by preventing the loss of circulation that will result in serious nerve damage.

Diabetic patients are also twice as likely to have a heart attack or stroke. This is because diabetes worsens atherosclerosis, a condition in which arteries narrow. High blood sugar levels have two effects on cells lining blood vessels. First, it increases the production of free radicals, highly reactive molecules that damage sensitive cell components like DNA, causing premature cell death (apoptosis). Second, it reduces the availability of nitric oxide (NO), which would otherwise enable blood vessels to relax and blood flow to increase. In patients without diabetes, fast blood flow triggers a cascade which leads to dilation of blood vessels and reduced inflammation. The diabetic patient does not have the benefit of such triggering due to the reduction in blood flow, which in turn worsens the condition.

Therefore the diabetic patient may be beneficially treated by increasing blood flow to areas of the body by stimulating associated dorsal root ganglions as described above. In particular, such increase in blood flow may reduce the incidence of nerve damage, heart attack and stroke in those suffering from diabetes.

Peripheral Vascular Disease

Peripheral vascular disease (PVD), refers to the obstruction of large arteries in the periphery of the vascular system. PVD causes either acute or chronic ischemia (lack of blood supply). PVD also includes a subset of diseases classified as microvascular diseases resulting from episodal narrowing of the arteries (Raynaud's phenomenon), or widening thereof (erythromelalgia). For the patient, PVD can manifest as claudication (pain, weakness, numbness, or cramping in muscles due to decreased blood flow), sores, wounds, or ulcers that heal slowly or not at all, noticeable changes in skin color (blueness or paleness) or temperature (coolness) when compared to the other limbs, or diminished hair and nail growth on affected limb and digits, to name a few. Individuals with PVD may require amputation and can have an elevated risk for cardiovascular events and eventual death of a cardiac or cerebrovascular etiology. Thus, patients suffering from peripheral vascular disease may be beneficially treated by increasing blood flow to portions of the peripheral vascular system by stimulating associated dorsal root ganglions as described above.

Limb Ischemia

Limb ischemia is an obstruction of the arteries that seriously decreases blood flow to the extremities (hands, feet and legs) and has progressed to the point of severe pain and even skin ulcers or sores. Limb ischemia is often present in people suffering from severe cases of peripheral vascular disease. However, there are a variety of risk factors for developing the disease, including age, smoking, diabetes, obesity, sedentary lifestyle, high cholesterol, high blood pressure, and family history of atherosclerosis or claudication. Thus, patients suffering from limb ischemia for any reason may be beneficially treated by increasing blood flow to the limb by stimulating associated dorsal root ganglions as described above.

Myocardial Ischemia

Myocardial Ischemia develops when coronary blood flow becomes inadequate to meet myocardial oxygen demand. In some instances, myocardial ischemia results from abnormal constriction or deficient relaxation of coronary microcirculation (ie, resistance vessels). Coronary spasm can also reduce coronary flow reserve significantly by causing dynamic stenosis of coronary arteries. Myocardial ischemia causes myocardial cells to switch from aerobic to anaerobic metabolism, with a progressive impairment of metabolic, mechanical, and electrical functions. Angina pectoris, often described as severe chest pain, is a common clinical manifestation of myocardial ischemia. It is caused by chemical and mechanical stimulation of sensory afferent nerve endings in the coronary vessels and myocardium. These nerve fibers extend from the first to fourth thoracic spinal nerves, ascending via the spinal cord to the thalamus, and from there to the cerebral cortex.

The heart and coronary arteries are innervated by sympathetic afferent fibers that have their cell bodies concentrated in the dorsal root ganglia of the T2 to T6 spinal segments but can extend as far as the C8 to T9 segments. Dorsal root ganglion cells have axons that enter the tract of Lissauer and terminate in the same segment, or the axons can ascend and descend a few segments before terminating in the spinal gray matter. Patients suffering from myocardial ischemia may be beneficially treated by increasing blood flow in the coronary vascular system by stimulating associated dorsal root ganglions as described above. Likewise, patients presenting with angina pectoris may be beneficially treated for pain symptoms by stimulating associated dorsal root ganglions as described above.

Stroke

Initial treatment for a stroke varies depending on whether it is an ischemic stroke (caused by a blood clot) or a hemorrhagic stroke (caused by bleeding in the brain). For an ischemic stroke, initial treatment focuses on restoring blood flow. Permanent damage from a stroke often occurs within the first few hours so swift restoration of blood flow will lessen damage that will occur. Current treatments include a clot-dissolving medicine called tissue plasminogen activator (t-PA), which can increase chances of survival and recovery. In addition, the patient may receive aspirin or aspirin combined with another antiplatelet medicine. However, aspirin is not recommended within 24 hours of treatment with t-PA. Other medicines may be given to control blood sugar levels, fever, and seizures. Patients suffering from an ischemic stroke may be beneficially treated by quickly restoring blood flow to the brain by stimulating associated dorsal root ganglions as described above.

Erectile Dysfunction

Erectile dysfunction is a sexual dysfunction characterized by the inability to develop or maintain an erection of the penis. A penile erection is the hydraulic effect of blood entering and being retained in sponge-like bodies within the penis. Thus, there are a variety of circulatory causes of erectile dysfunction. The most common circulatory causes are cardiovascular disease and diabetes. By treating these circulatory maladies with the devices, systems and methods described herein, erectile dysfunction may be prevented or treated.

Sympathetically Mediated Pain

Sympathetically mediated pain and sympathetically maintained pain refers to pain signals that are transmitted to the brain from the sympathetic nervous system, the part of the nervous system controlling 'involuntary' functions of the body such as heart rate, sweating, constriction of blood vessels, and digestion. In certain abnormal situations the pain signals from the sympathetic nervous system become constant and severe, even though there is no obvious cause of pain. The mechanism by which this happens is complex and not fully understood.

Sympathetic pain usually has a severe, burning characteristic and often begins in the hand or foot. The affected area is very hypersensitive to even the lightest touch. Pink or bluish discoloration of the involved area may occur because of abnormal circulation, and abnormal sweating may also be noticed. There are a number of diagnostic phrases used by physicians when discussing sympathetic pain syndromes. In the past the most commonly used phrase was Reflex Sympathetic Dystrophy, or RSD. Other terms used to describe the condition include causalgia and sympathetically mediated pain. Recently, "Chronic Regional Pain Syndrome" or CRPS has become commonly used. Such sympathetic pain can also be treated by selective stimulation of one or more dorsal root ganglions since sympathetic afferents can travel through the DRG. In some embodiments, a negative feedback loop on efferent sympathetic activity is created. And, in other embodiments, a stellate ganglion blockade is used in treating certain pain conditions.

Thus, blood vessels are just one of many targets that can be influenced by affecting the sympathetic nervous system via selective stimulation of one or more dorsal root ganglions. A variety of other end organs may also be influenced by selective stimulation of one or more dorsal root ganglions to treat medical conditions associated with these end organs. For example, the lungs may be influenced in the treatment patients suffering from constriction of air passages. There are a variety of circumstances and conditions that cause the bronchi of the lungs to become narrow, or constrict, making it difficult to breathe. Bronchoconstriction, or the narrowing of the airways, is typically caused by the muscles surrounding the lungs becoming tight. A build-up of excess mucous as well as inflammation can also cause constriction. The constriction results in coughing, wheezing and shortness of breath. There are several conditions that cause this; such conditions include but are not limited to: Chronic lung disease (CLD), Emphysema, Exercise-Induced bronchoconstriction, Allergen-induced bronchoconstriction, and Asthma. In some embodiments, bronchodilation, the process by which the bronchi (tubes in the lungs made of connective tissue and muscle) are dilated, or opened, is achieved by selective stimulation of one or more dorsal root ganglions.

It is known that bronchodilation can occur as part of the body's natural response. When the sympathetic nervous system is activated in what is commonly known as the "fight or flight" response, the hormones and neurotransmitters of adrenaline (also called epinephrine) and noradrenaline (also called norepinephrine) are released. This response can be naturally triggered by physical or mental stress. And, aspects of this natural response can be harnessed to treat patients suffering from bronchoconstriction. In particular, one or more dorsal root ganglia associated with portions of the sympathetic nervous system involved in bronchodilation are selectively stimulated using the devices, systems and method described and referenced herein. Such selective stimulation leads to desired bronchodilation in treatment of the medical condition suffered by the patient.

Figure 5:
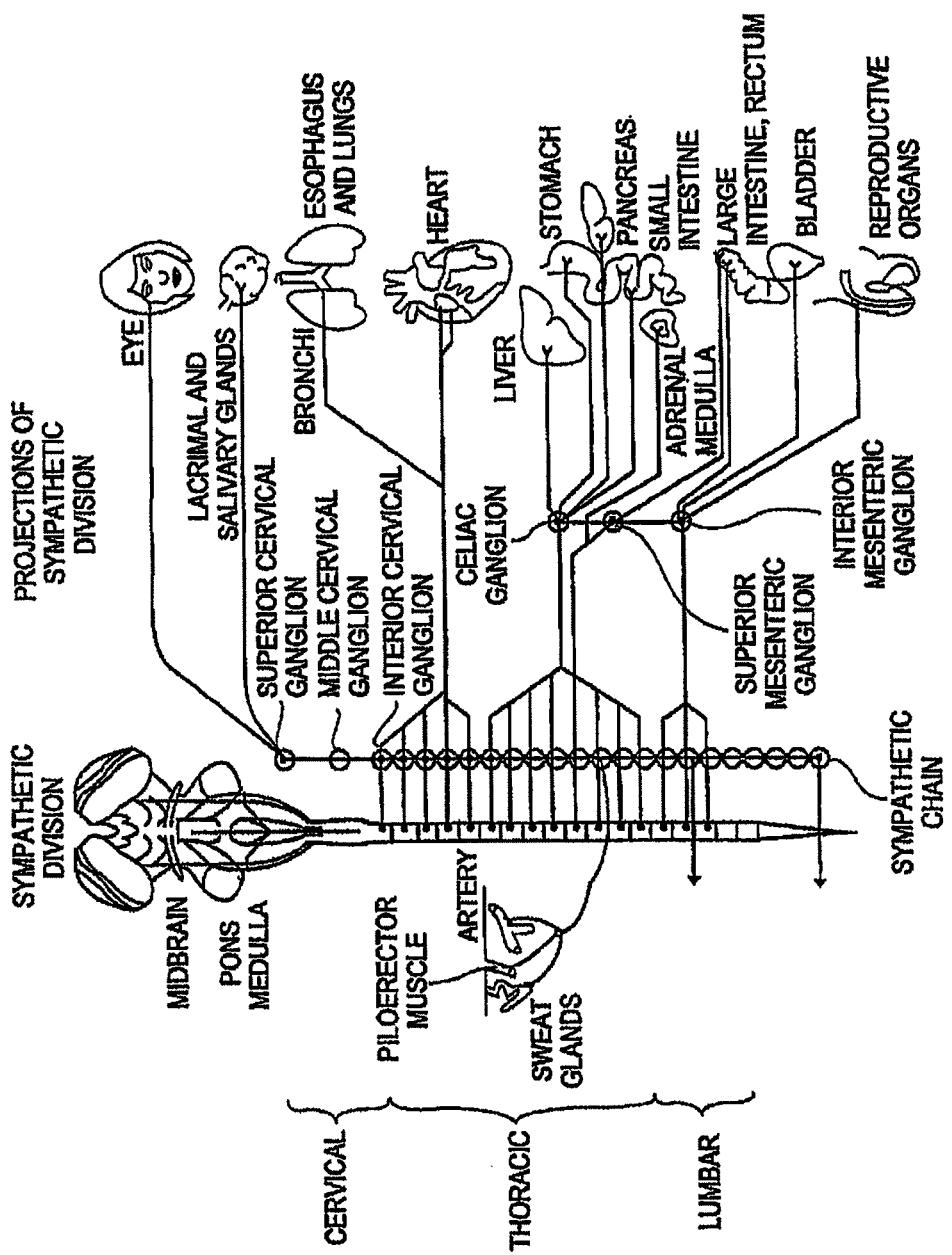
FIG. 5 is a schematic illustration of a portion the sympathetic nervous system.

As mentioned, a variety of end organs may also be influenced by selective stimulation of one or more dorsal root ganglions to treat medical conditions associated with these end organs. FIG. 5 is a schematic illustration of a portion of the sympathetic nervous system and associated target organs and tissues that can be influenced. As shown, each sympathetic ganglion SG along the sympathetic chain is associated with a spinal level, in particular, a dorsal root ganglion on a spinal level. And, one or more sympathetic ganglions SG are associated with a particular organ, system or tissue, such as the heart, liver or stomach, to name a few. It may be appreciated that stimulation of one or more dorsal root ganglions may alternatively or additionally influence other ganglions, such as mesenteric ganglions, celiac ganglions, stellate ganglions and cervical ganglions, to name a few. These ganglions in turn affect particular organs, systems or tissues.

Figure 6:
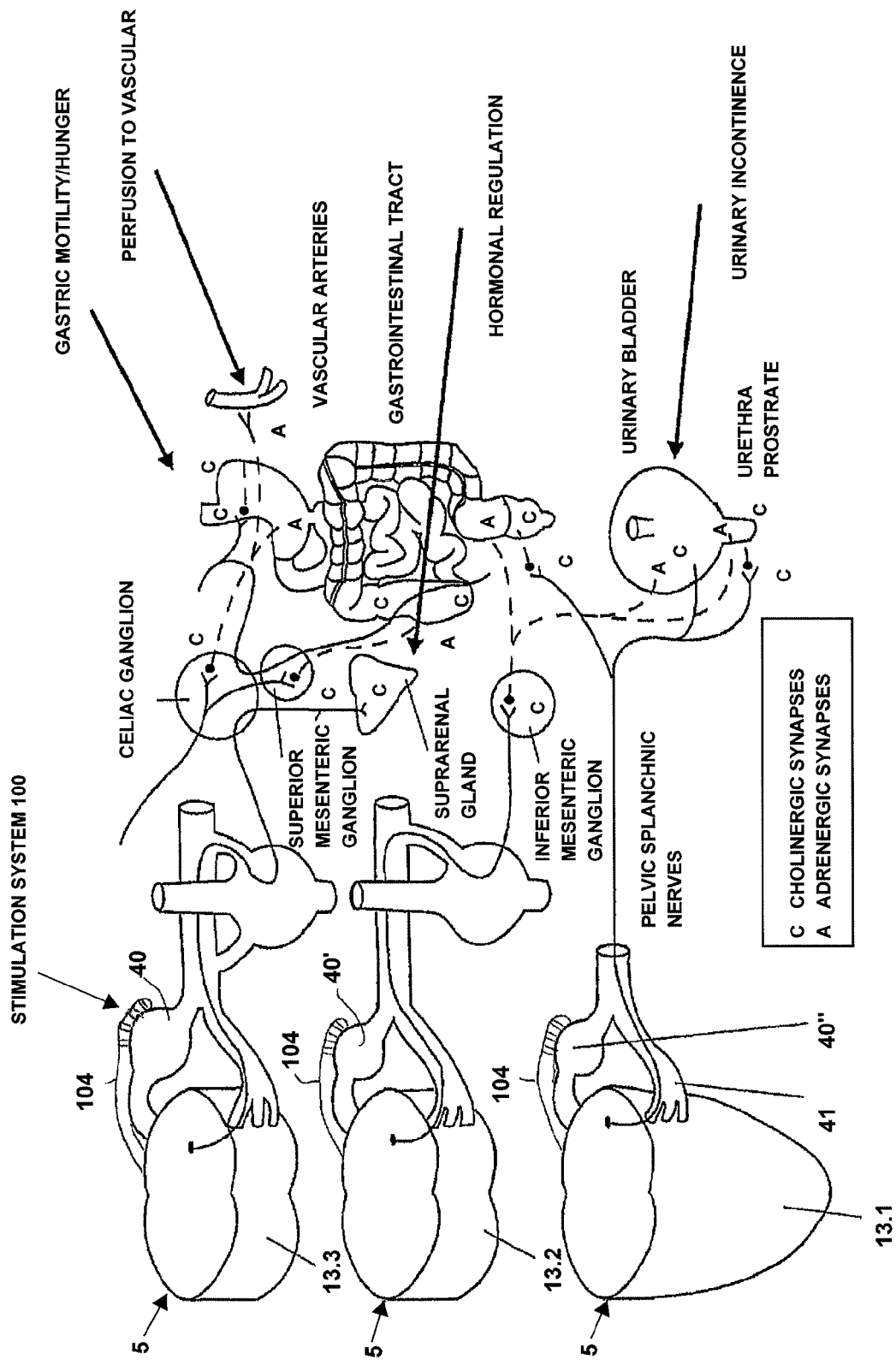
FIG. 6 is an illustration of a portion of sympathetic nervous system neuromodulated by an embodiment of the present invention.

FIG. 6 illustrates how embodiments of the present invention may be advantageously utilized for neurostimulation of the sympathetic chain using direct stimulation of an associated DRG. This aspect of the present invention takes advantage of the anatomical placement of the DRG relative to the sympathetic chain in conjunction with gate control theory to direct DRG stimulation for control of the sympathetic system. Thus, selective neurostimulation techniques of the present invention may be advantageously employed to, for example, provide and/or augment therapeutic tools in regards to weight control, hormonal regulation, vascular perfusion, etc. Additional alternative embodiments include the use of specific stimulation to provide organ system autonomic modulation. Through implantation of stimulation electrodes and systems of the present invention to stimulate the appropriate DRG upstream of the associated portion(s) of the sympathetic chain, the associated system may be controlled, modulated or influenced utilizing the electrical and/or pharmacological agent stimulation techniques described herein. Thus, there is provided a method of modulating a neural pathway in the sympathetic nervous system by stimulating a spinal dorsal root ganglion upstream of at least one ganglion of the sympathetic nerve chain to influence a condition associated with the at least one ganglion of the sympathetic nerve chain.

In one specific example, by stimulating the DRG 40 associated with spinal level 13.3, as shown in FIG. 6, the portion of the sympathetic chain associated with hormonal regulation may be altered, modified, influenced or controlled. Similarly, by stimulating the DRG 40' associated with spinal level 13.2 and/or the DRG 40" associated with level 13.1, the portion of the sympathetic chain associated with the gastrointestinal tract, or urinary incontinence (i.e., urinary bladder, urethra, prostate, etc.) may be altered, modified, influenced or controlled.

Figure 7:
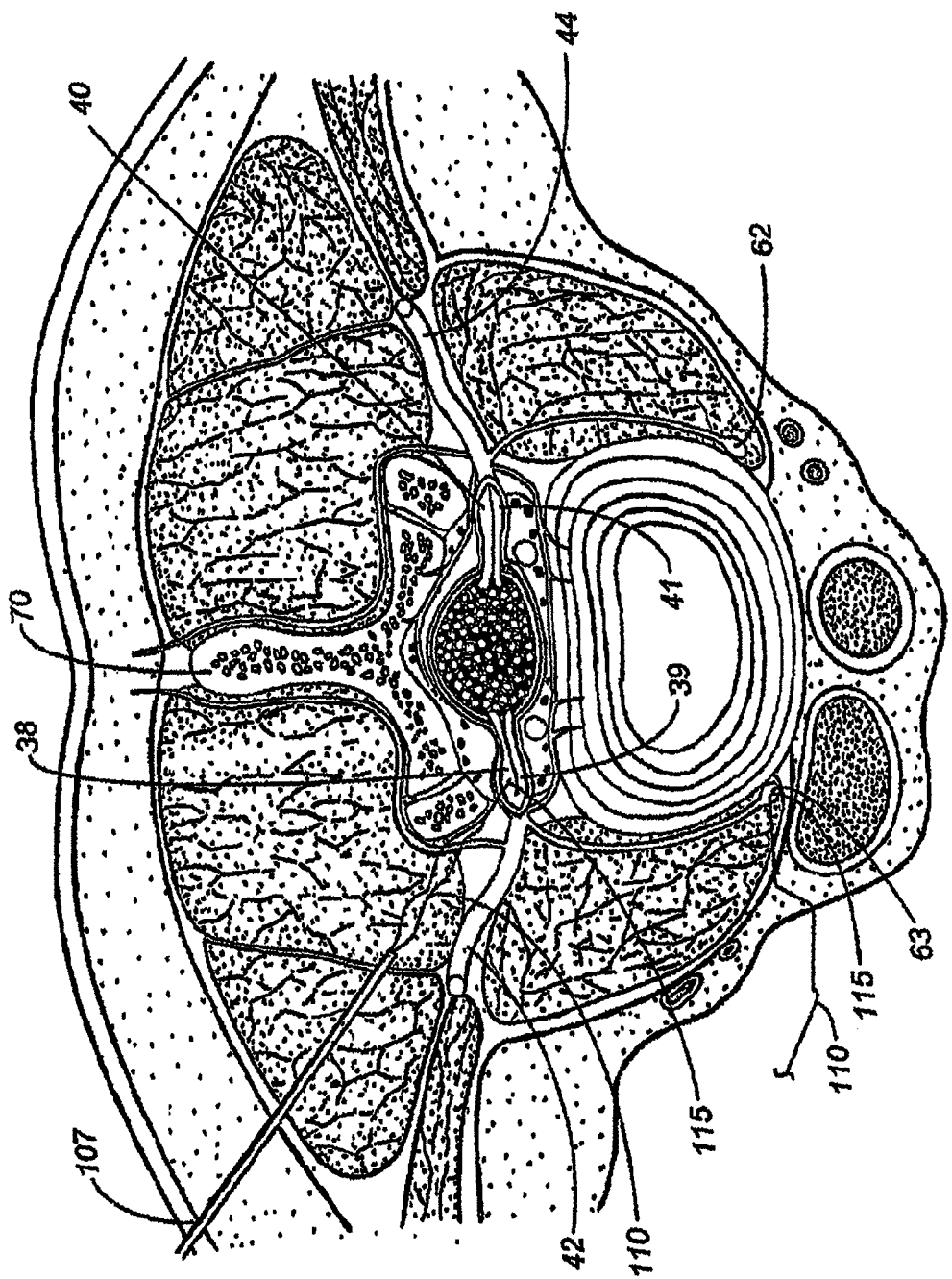
FIG. 7 is an illustration of embodiments of the present invention implanted for the direct stimulation of a single sympathetic nerve ganglion and a single dorsal root ganglion on the same spinal level.

Optionally or additionally, the direct stimulation techniques described herein may be used to directly stimulate individual nerve ganglion of the sympathetic nervous system, such as, for example, the celiac ganglion, superior mesenteric ganglion, inferior mesenteric ganglion and others listed in FIGS. 5, 6 or known to those of ordinary skill. It is to be appreciated that the stimulation systems, pulse generators, leads, electrodes, and/or microelectrodes and other components are modified and sized as needed to allow for direct stimulation of the ganglion including implanting into the ganglion or within adjacent nerve sheaths leading to the ganglion. FIG. 7 illustrates an embodiment of a combined direct stimulation of a DRG 38 with microelectrode 115 as well as a suitably sized microelectrode 115 implanted in a sympathetic nerve root ganglion 63. The electrodes in FIG. 7 may stimulate independently or in a coordinated fashion to achieve the desired clinical outcome or other desired result. Similar to the discussion above for electrode placement in, on or about the DRG, electrode placement for the sympathetic chain may also be unilateral, bilateral, on adjacent portions of the chain or separate portions of the chain as needed.

One aspect of the present invention is a method of modulating a neural pathway in the sympathetic nervous system including stimulating a spinal dorsal root ganglion upstream of at least one ganglion of the sympathetic nerve chain to influence a condition associated with the at least one ganglion of the sympathetic nerve chain. In one specific embodiment, stimulating a spinal dorsal root ganglion comprises stimulating a spinal dorsal root ganglion upstream of at least one ganglion of the sympathetic nerve chain to influence functional activation of a bodily system associated with the at least one ganglion along the sympathetic nerve chain, to influence functional activation of an organ associated with the at least one ganglion along the sympathetic nerve chain, or to influence functional inhibition of a bodily system associated with the at least one ganglion along the sympathetic nerve chain. In specific embodiments, the ganglion of the sympathetic nerve chain is a cervical ganglion, a thoracic ganglion, a lumbar ganglion or a sacral ganglion.

It may be appreciated that embodiments of the present invention may be used in conjunction with other neurostimulation techniques by combining an upstream stimulation using specific DRG stimulation of the present invention with another stimulation acting downstream of the DRG stimulation. As used herein, downstream and upstream refer to pathways closer to the brain (i.e., upstream) or further from the brain (i.e., downstream). For example, several stimulation techniques are described by Rezai in US Patent Publication 2002/0116030 and U.S. Pat. No. 6,438,423 and by Dobak in publication 2003/0181958, all of which are incorporated herein by reference. In specific aspects, embodiments of the present invention may be used to provide electrical and combinational (i.e., with a pharmacological agent) stimulation of the sympathetic nerve chain as described by Rezai alone (i.e., using the appropriate DRG stimulation or implanting directly into a nerve root ganglion). Alternatively or additionally, embodiments of the present invention provide specific, direct stimulation of one or more DRG and are used in combination with the stimulation techniques described by Rezai (i.e., conventional stimulation of the sympathetic chain using one or more of Rezai's techniques).

Referring back to FIG. 1, in some embodiments, the implantable pulse generator (IPG) 102 comprises circuitry which initiates or modifies the electrical stimulation in response to one or more sensors. Example sensors include, among others, blood glucose sensors, blood pressure sensors, blood flow sensors (including Doppler and other techniques), heart rate sensors, blood oxygen sensors, temperature sensors, accelerometers, strain gauges, electrocardiograms, brain wave detectors (electroencephalograms, other interiorly and exteriorly measured composite neuronal activity), electrical devices which measure electrical activity in muscles and/or nerves, or other devices capable of measuring physiological parameters indicative of symptoms of the disorder under treatment.

In some embodiments, the one or more sensors sense the status of one or more symptoms of the disorder. Such status information is utilized to modify the electrical stimulation to a level which is appropriate to improve status of the disorder in real time. This modification of electrical stimulation may be particularly beneficial in the treatment of conditions which have a time dependency, such as stroke.

In some embodiments, the sensor detects one or more of the following functions or aspect of the body: carbon dioxide pressure in a target tissue, action potential conduction (such as in a target nerve), body movement, balance, motor activity including muscle tone, heart rate, blood pressure, capillary pressure, venous pressure, arterial pressure, blood flow, circulation (including blood and lymphatic), perfusion, electrocardiogram, oxygenation (including blood oxygenation levels, oxygen saturation levels, oxygen consumption, oxygen pressure), concentration of certain biological molecules/substances in the body (such as, for example, glucose, liver enzymes, electrolytes, hormones, creatinine, medications, concentration of various cells, platelets, or bacteria), pH levels, chemical production, neurotransmitter levels, electrolyte levels in the circulation/tissue, nitrogen pressure, respiratory function, chest wall expansion, diaphragmatic movement, cognitive activity, electroencephalogram, flushing, galvanic skin responses, perspiration, body temperature regulation, response to external stimulation, pain, speech, temperature, visual activity, intra-bladder pressure, and water pressure.

In some embodiments, the sensor is positioned so as to measure sympathetic nerve outflow. In such embodiments, the sensor may be positioned on or near the sympathetic chain.

In some embodiments, the implantable pulse generator (IPG) 102 comprises circuitry which initiates or modifies the electrical stimulation in response to a timer or clock. Thus, stimulation may be reduced or eliminated during times in which it is determined that the patient desires reduced or no treatment. Such periods of reduced usage may extend the life of the power supply 110.

Although the foregoing invention has been described in some detail by way of illustration and example, for purposes of clarity of understanding, it will be obvious that various alternatives, modifications, and equivalents may be used and the above description should not be taken as limiting in scope of the invention which is defined by the appended claims.

INCORPORATION BY REFERENCE

All publications and patent applications mentioned in this specification are herein incorporated by reference to the same extent as if each individual publication or patent application was specifically and individually indicated to be incorporated by reference.

What is claimed is:

1. A method of treating myocardial ischemia in a patient by modulating a neural pathway in the sympathetic nervous system, comprising:
    identifying myocardial ischemia in the patient;
    positioning at least one electrode on a dorsal root ganglion epinurium in close proximity to the dorsal root ganglion of the patient upstream of at least one ganglion of the sympathetic nerve chain, wherein the dorsal root ganglion is located within T2 to T6 spinal segments; and
    treating myocardial ischemia in the patient by increasing blood flow in the coronary vascular system through provision of electrical pulses to the at least one electrode so as to directly neuromodulate the dorsal root ganglion in a manner that influences a condition associated with the at least one ganglion of the sympathetic nerve chain while excluding neuromodulation of an associated ventral root.

2. The method of claim 1 wherein the treating is applied when the patient is experiencing an episode of angina pectoris.

3. The method of claim 1 wherein the treating is applied when the patient is experiencing an episode of coronary spasm.

4. The method according to claim 1 further comprising directly applying stimulation to the at least one ganglion along the sympathetic nerve chain.

5. The method according to claim 4 wherein the directly applying stimulation step for the at least one ganglion along the sympathetic nerve chain is performed using an electrode exposed to the at least one ganglion along the sympathetic nerve chain.

6. The method of claim 1 wherein the positioning comprises implanting the at least one electrode through an epidural space of the patient through a foramen into position in close proximity to the dorsal root ganglion.

7. The method of claim 1 wherein the positioning comprises implanting the at least one electrode without entry into the spinal column of the patient.

8. The method of claim 1 further comprising:
    employing a sensor to sense a physiological condition of the patient relevant to myocardial ischemia in the patient to control application of stimulation pulses to the dorsal root ganglion.

9. The method of claim 8 wherein the sensor generates a signal indicative of one item selected from the list consisting of: heart rate, blood pressure, arterial pressure, blood flow, cardiac perfusion, electrocardiogram activity, and blood oxygenation.

* * * * *